(12) United States Patent
Renold et al.

(10) Patent No.: US 8,623,896 B2
(45) Date of Patent: Jan. 7, 2014

(54) INSECTICIDAL COMPOUNDS

(75) Inventors: Peter Renold, Stein (CH); Werner Zambach, Stein (CH); Peter Maienfisch, Stein (CH); Michel Muehlebach, Stein (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 611 days.

(21) Appl. No.: 12/810,478

(22) PCT Filed: Dec. 16, 2008

(86) PCT No.: PCT/EP2008/010701
§ 371 (c)(1),
(2), (4) Date: Jun. 24, 2010

(87) PCT Pub. No.: WO2009/080250
PCT Pub. Date: Jul. 2, 2009

(65) Prior Publication Data
US 2010/0279999 A1 Nov. 4, 2010

(30) Foreign Application Priority Data

Dec. 24, 2007 (GB) .................................. 0725219.0
Jul. 29, 2008 (GB) .................................. 0813849.7

(51) Int. Cl.
*A61K 31/42* (2006.01)
*A61K 31/38* (2006.01)
*C07D 261/02* (2006.01)
*C07D 331/04* (2006.01)
*A01N 31/00* (2006.01)
*A01N 33/00* (2006.01)

(52) U.S. Cl.
USPC ........... 514/378; 514/359; 514/430; 548/240; 549/88

(58) Field of Classification Search
None
See application file for complete search history.

(56) References Cited

U.S. PATENT DOCUMENTS

2007/0066617 A1* 3/2007 Mita et al. ..................... 514/241

FOREIGN PATENT DOCUMENTS

| EP | 1731512 | 12/2006 |
| WO | 2007026965 | 3/2007 |
| WO | 2008016811 | 2/2008 |

* cited by examiner

*Primary Examiner* — Brandon Fetterolf
*Assistant Examiner* — Theodore R West
(74) *Attorney, Agent, or Firm* — R. Kody Jones

(57) ABSTRACT

A compound of formula (I), wherein $A^1$, $A^2$, $A^3$, $A^4$, $G^1$, L, $R^1$, $R^2$, $R^3$, $R^4$, $Y^1$, $Y^2$ and $Y^3$ are as defined in claim 1; or a salt or N-oxide thereof. Furthermore, the present invention relates to processes and intermediates for preparing compounds of formula (I), to insecticidal, acaricidal, molluscicidal and nematicidal compositions comprising them and to methods of using them to combat and control insect, acarine, mollusc and nematode pests.

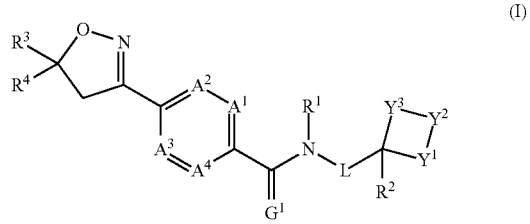

(I)

21 Claims, No Drawings

INSECTICIDAL COMPOUNDS

This application is a 371 of International Application No. PCT/EP2008/010701 filed Dec. 16, 2008, which claims priority to GB 0725219.0 filed Dec. 24, 2007, and GB 0813849.7 filed Jul. 29, 2008, the contents of which are incorporated herein by reference.

The present invention relates to certain benzamide isoxazolines, to processes and intermediates for preparing them, to insecticidal, acaricidal, molluscicidal and nematicidal compositions comprising them and to methods of using them to combat and control insect, acarine, mollusc and nematode pests.

Certain isoxazoline derivatives with insecticidal properties are disclosed, for example, in EP 1,731,512, US 2007/066617, JP 2007/008914, JP 2007/016017, EP 1,932,836, JP 2007/106756, WO 07/070606, EP 1,975,149 and WO 07/075459.

It has now surprisingly been found that certain benzamide isoxazolines have insecticidal properties.

The present invention therefore provides a compound of formula (I)

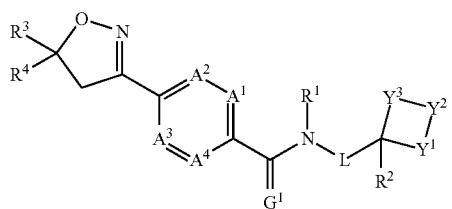

wherein
$A^1$, $A^2$, $A^3$ and $A^4$ are independently of one another C—H, C—$R^5$, or nitrogen;
$G^1$ is oxygen or sulfur;
L is a single bond, $C_1$-$C_8$alkyl, $C_1$-$C_8$haloalkyl, $C_2$-$C_8$alkenyl, $C_2$-$C_8$haloalkenyl, $C_2$-$C_8$alkynyl, or $C_2$-$C_8$haloalkynyl;
$R^1$ is hydrogen, $C_1$-$C_8$alkyl, $C_1$-$C_8$alkylcarbonyl-, or $C_1$-$C_8$alkoxycarbonyl-;
$R^2$ is hydrogen, or $C_1$-$C_8$alkyl;
$R^3$ is $C_1$-$C_8$haloalkyl;
$R^4$ is aryl or aryl substituted by one to three $R^6$, or heterocyclyl or heterocyclyl substituted by one to three $R^6$;
$Y^1$, $Y^2$ and $Y^3$ are independently of another $CR^7R^8$, C=O, C=N—$OR^9$, N—$R^9$, S, SO, $SO_2$, S=N—$R^9$, or SO=N—$R^9$, provided that at least one of $Y^1$, $Y^2$ or $Y^3$ is not $CR^7R^8$;
each $R^5$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, $C_1$-$C_8$alkoxycarbonyl-, aryl or aryl optionally substituted by one to three $R^{10}$, or heteroaryl or heteroaryl optionally substituted by one to three $R^{10}$, or where two $R^5$ are adjacent, the two $R^5$ may together with the carbon atoms to which the two $R^5$ are bonded form a 5-membered ring, wherein the 5-membered ring is —OCH=N—, —SCH=N—, —OCR$^{10}$=N—, or —SCR$^{10}$=N—; each $R^6$ is independently halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl-;
each $R^7$ and $R^8$ is independently hydrogen, halogen, $C_1$-$C_8$alkyl, or $C_1$-$C_8$haloalkyl;
each $R^9$ is independently hydrogen, cyano, nitro, $C_1$-$C_8$alkyl, $C_1$-$C_8$haloalkyl, $C_1$-$C_8$alkylcarbonyl-, $C_1$-$C_8$haloalkylcarbonyl-, $C_1$-$C_8$alkoxycarbonyl-, $C_1$-$C_8$haloalkoxycarbonyl-, $C_1$-$C_8$alkylsulfonyl-, $C_1$-$C_8$haloalkylsulfonyl-, aryl-$C_1$-$C_4$alkyl- or aryl-$C_1$-$C_4$alkyl- wherein the aryl moiety is substituted by one to three $R^{11}$, or heteroaryl-$C_1$-$C_4$alkyl- or heteroaryl-$C_1$-$C_4$alkyl- wherein the heteroaryl moiety is substituted by one to three $R^{11}$;
each $R^{10}$ is independently halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl-; and
each $R^{11}$ is independently halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl-; or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

The compounds of the invention may contain one or more asymmetric carbon atoms, for example, in the —$CR^3R^4$— group or at the $LR^2Y^1Y^3$ carbon and may exist as enantiomers (or as pairs of diastereoisomers) or as mixtures of such. Further, where any Y group is SO, the compounds of the invention are sulfoxides, which can also exist in two enantiomeric forms.

Each alkyl moiety either alone or as part of a larger group (such as alkoxy, alkylcarbonyl, or alkoxycarbonyl) is a straight or branched chain and is, for example, methyl, ethyl, n-propyl, prop-2-yl, n-butyl, but-2-yl, 2-methyl-prop-1-yl or 2-methyl-prop-2-yl. The alkyl groups are preferably $C_1$ to $C_6$ alkyl groups, more preferably $C_1$-$C_4$ and most preferably $C_1$-$C_3$ alkyl groups.

Alkenyl moieties can be in the form of straight or branched chains, and the alkenyl moieties, where appropriate, can be of either the (E)- or (Z)-configuration. Examples are vinyl and allyl. The alkenyl groups are preferably $C_2$-$C_6$, more preferably $C_2$-$C_4$ and most preferably $C_2$-$C_3$ alkenyl groups.

Alkynyl moieties can be in the form of straight or branched chains. Examples are ethynyl and propargyl. The alkynyl groups are preferably $C_2$-$C_6$, more preferably $C_2$-$C_4$ and most preferably $C_2$-$C_3$ alkynyl groups.

Halogen is fluorine, chlorine, bromine or iodine.

Haloalkyl groups (either alone or as part of a larger group, such as haloalkoxy) are alkyl groups which are substituted by one or more of the same or different halogen atoms and are, for example, trifluoromethyl, chlorodifluoromethyl, 2,2,2-trifluoro-ethyl or 2,2-difluoro-ethyl.

Haloalkenyl groups are alkenyl groups, respectively, which are substituted with one or more of the same or different halogen atoms and are, for example, 2,2-difluorovinyl or 1,2-dichloro-2-fluoro-vinyl.

Haloalkynyl groups are alkynyl groups, respectively, which are substituted with one or more of the same or different halogen atoms and are, for example, 1-chloro-prop-2-ynyl.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

The term "heteroaryl" refers to an aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl, and thiadiazolyl. Examples of bicyclic groups include quinolinyl, cinnolinyl, quinoxalinyl, benzimidazolyl, benzothiophenyl, and benzothiadiazolyl. Monocyclic heteroaryl groups are preferred, pyridyl being most preferred.

The term "heterocyclyl" is defined to include heteroaryl and in addition their unsaturated or partially unsaturated analogues.

Preferred values of $A^1, A^2, A^3, A^4, G^1, L, R^1, R^2, R^3, R^4, Y^1, Y^2, Y^3, R^5, R^6, R^7, R^8, R^9, R^{10}$, and $R^{11}$, are, in any combination, as set out below.

Preferably no more than two of $A^1$, $A^2$, $A^3$ and $A^4$ are nitrogen.

Preferably $A^1$ is C—H or C—$R^5$, most preferably $A^1$ is C—$R^5$.

Preferably $A^2$ is C—H or C—$R^5$, most preferably $A^2$ is C—H.

Preferably $A^3$ is C—H or C—$R^5$, most preferably $A^3$ is C—H.

Preferably $A^4$ is C—H or C—$R^5$, most preferably $A^4$ is C—H.

Preferably $G^1$ is oxygen.

Preferably L is a single bond, $C_1$-$C_8$alkyl, or $C_1$-$C_8$haloalkyl, more preferably a single bond, or $C_1$-$C_8$alkyl, even more preferably a single bond or $C_1$-$C_2$alkyl, yet even more preferably a single bond or methyl, most preferably a single bond.

Preferably $R^1$ is hydrogen, methyl, ethyl, methylcarbonyl-, or methoxycarbonyl-, more preferably hydrogen, methyl or ethyl, even more preferably hydrogen or methyl, most preferably hydrogen.

Preferably $R^2$ is hydrogen or methyl, most preferably hydrogen.

Preferably $R^3$ is chlorodifluoromethyl or trifluoromethyl, most preferably trifluoromethyl.

In one group of preferred compounds $R^4$ is aryl or aryl substituted by one to three $R^6$, more preferably $R^4$ is phenyl or phenyl substituted by one to three $R^6$, even more preferably $R^4$ is phenyl substituted by one to three $R^6$, more preferably $R^4$ is 3,5-bis-(trifluoromethyl)-phenyl, 3,5-dibromo-phenyl, 3,5-dichloro-phenyl, 3,4-dichloro-phenyl, 3-trifluoromethyl-phenyl, or 3,4,5-trichloro-phenyl, yet even more preferably $R^4$ is 3,5-dibromo-phenyl, 3,5-dichloro-phenyl, 3,4-dichloro-phenyl, or 3,4,5-trichloro-phenyl, most preferably $R^4$ is 3,5-dichloro-phenyl.

In another preferred group of compounds $R^4$ is heterocyclyl or heterocyclyl substituted by one to three $R^6$, more preferably $R^4$ is heteroaryl or heteroaryl substituted by one to three $R^6$, even more preferably $R^4$ is pyridyl or pyridyl substituted by one to three $R^6$, most preferably $R^4$ is pyridyl substituted by one to three $R^6$.

Preferably $Y^1$, $Y^2$ and $Y^3$ are independently of another $CR^7R^8, C=O, C=N-OR^9, N-R^9, S, SO, SO_2, S=N-R^9$, or $SO=N-R^9$, provided that one of $Y^1$, $Y^2$ or $Y^3$ is not $CR^7R^8$, more preferably $Y^1$, $Y^2$ and $Y^3$ are independently of another $CR^7R^8, N-R^9, S, SO, SO_2, S=N-R^9$, or $SO=N-R^9$, provided that one of $Y^1$, $Y^2$ or $Y^3$ is not $CR^7R^8$, even more preferably $Y^1$, $Y^2$ and $Y^3$ are independently of another $CR^7R^8$, S, SO, or $SO_2$, provided that one of $Y^1$, $Y^2$ or $Y^3$ is not $CR^7R^8$, most preferably $Y^2$ is S, SO, or $SO_2$, and $Y^1$ and $Y^3$ are independently of another $CR^7R^8$.

In one embodiment $Y^1$ is $C=O, C=N-OR^9, N-R^9, S, SO, SO_2, S=N-R^9$, or $SO=N-R^9$, and $Y^2$ and $Y^3$ are independently of another $CR^7R^8$.

In one embodiment $Y^2$ is $C=O, C=N-OR^9, N-R^9, S, SO, SO_2, S=N-R^9$, or $SO=N-R^9$, and $Y^1$ and $Y^3$ are independently of another $CR^7R^8$.

Preferably each $R^5$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-, more preferably halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl-, even more preferably bromo, chloro, fluoro, cyano, nitro, methyl, ethyl, trifluoromethyl, methoxy, difluoromethoxy, trifluoromethoxy, or methoxycarbonyl-, yet even more preferably bromo, chloro, fluoro, nitro, or methyl, most preferably chloro, fluoro, or methyl.

Preferably each $R^6$ is independently bromo, chloro, fluoro, cyano, nitro, methyl, ethyl, trifluoromethyl, methoxy, difluoromethoxy, trifluoromethoxy, or methoxycarbonyl-, more preferably chloro, fluoro, cyano, nitro, methyl, ethyl, trifluoromethyl, methoxy, or trifluoromethoxy, most preferably bromo, chloro, or fluoro.

Preferably each $R^7$ and $R^8$ is independently hydrogen or methyl, most preferably hydrogen.

Preferably each $R^9$ is independently hydrogen, cyano, methyl, trifluoromethyl, methylcarbonyl-, trifluoromethylcarbonyl-, methoxycarbonyl-, trifluoromethoxycarbonyl-, methylsulfonyl-, trifluoromethylsulfonyl-, or benzyl or benzyl wherein the phenyl moiety is substituted by one to three $R^{10}$, most preferably hydrogen, methyl, trifluoromethyl, or benzyl or benzyl wherein the phenyl moiety is substituted by one to three $R^{10}$.

Preferably each $R^{10}$ is independently bromo, chloro, fluoro, cyano, nitro, methyl, ethyl, trifluoromethyl, methoxy, difluoromethoxy, trifluoromethoxy, or methoxycarbonyl-, more preferably chloro, fluoro, cyano, nitro, methyl, ethyl, trifluoromethyl, methoxy, or trifluoromethoxy, most preferably bromo, chloro, or fluoro.

Preferably each $R^{11}$ is independently bromo, chloro, fluoro, cyano, nitro, methyl, ethyl, trifluoromethyl, methoxy, difluoromethoxy, trifluoromethoxy, or methoxycarbonyl-, more preferably chloro, fluoro, cyano, nitro, methyl, ethyl, trifluoromethyl, methoxy, or trifluoromethoxy, most preferably bromo, chloro, or fluoro.

A preferred embodiment are compounds of formula (Ia) wherein $A^1$ is C—$R^5$, $A^2$, $A^3$, and $A^4$ are C—H, $R^4$ is 3,5-dichloro-phenyl, L is a bond, and $G^1$, $R^1$, $R^2$, $R^3$, $Y^1$, $Y^2$, and $Y^3$ are as defined for a compound of formula (I); or a salt or N-oxide thereof.

A preferred embodiment are compounds of formula (Ia.A) wherein $A^1$ is C—Br, $A^2$, $A^3$, and $A^4$ are C—H, $R^4$ is 3,5-dichloro-phenyl, L is a bond, and $G^1$, $R^1$, $R^2$, $R^3$, $Y^1$, $Y^2$, and $Y^3$ are as defined for a compound of formula (I); or a salt or N-oxide thereof.

A preferred embodiment are compounds of formula (Ia.B) wherein $A^1$ is C—CN, $A^2$, $A^3$, and $A^4$ are C—H, $R^4$ is 3,5-dichloro-phenyl, L is a bond, and $G^1$, $R^1$, $R^2$, $R^3$, $Y^1$, $Y^2$, and $Y^3$ are as defined for a compound of formula (I); or a salt or N-oxide thereof.

A preferred embodiment are compounds of formula (Ia.C) wherein $A^1$ is C-Me, $A^2$, $A^3$, and $A^4$ are C—H, $R^4$ is 3,5-dichloro-phenyl, L is a bond, and $G^1$, $R^1$, $R^2$, $R^3$, $Y^1$, $Y^2$, and $Y^3$ are as defined for a compound of formula (I); or a salt or N-oxide thereof.

A preferred embodiment are compounds of formula (Ia.D) wherein $A^1$ is C—$CF_3$, $A^2$, $A^3$, and $A^4$ are C—H, $R^4$ is 3,5-dichloro-phenyl, L is a bond, and $G^1$, $R^1$, $R^2$, $R^3$, $Y^1$, $Y^2$, and $Y^3$ are as defined for a compound of formula (I); or a salt or N-oxide thereof.

A preferred embodiment are compounds of formula (Ib) wherein $A^1$ is C—$R^5$, $A^2$, $A^3$, and $A^4$ are C—H, $R^4$ is 3,5-dichloro-phenyl, L is $CH_2$, and $G^1$, $R^1$, $R^2$, $R^3$, $Y^1$, $Y^2$, and $Y^3$ are as defined for a compound of formula (I); or a salt or N-oxide thereof.

Certain intermediates are novel and as such form a further aspect of the invention. One group of novel intermediates are compounds of formula (XI)

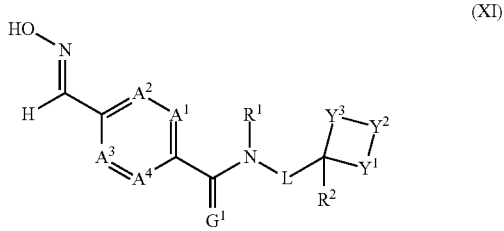

(XI)

wherein $A^1, A^2, A^3, A^4, G^1, L, R^1, R^2$, and $Y^3$ are as defined for a compound of formula (I); or a salt or N-oxide thereof. The preferences for $A^1, A^2, A^3, A^4, G^1, L, R^1, R^2, Y^1, Y^2$ and $Y^3$ are the same as the preferences set out for the corresponding substituents of a compound of formula (I).

Another group of novel intermediates are compounds of formula (XI')

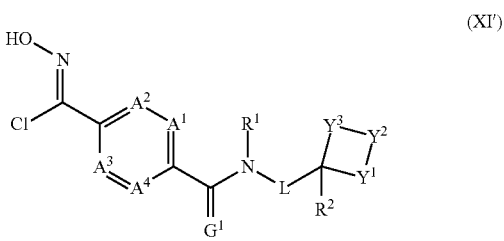

(XI')

wherein $A^1, A^2, A^3, A^4, G^1, L, R^1, R^2, Y^1, Y^2$ and $Y^3$ and $Y^3$ are as defined for a compound of formula (I); or a salt or N-oxide thereof. The preferences for $A^1, A^2, A^3, A^4, G^1, L, R^1, R^2, Y^1, Y^2$ and $Y^3$ are the same as the preferences set out for the corresponding substituents of a compound of formula (I).

Another group of novel intermediates are compounds of formula (XII)

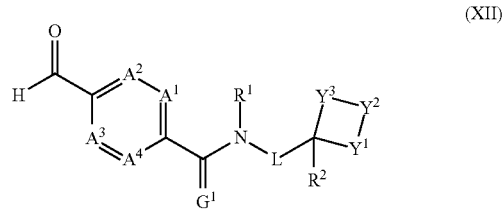

(XII)

wherein $A^1, A^2, A^3, A^4, G^1, L, R^1, R^2, Y^1, Y^2$ and $Y^3$ are as defined for a compound of formula (I); or a salt or N-oxide thereof. The preferences for $A^1, A^2, A^3, A^4, G^1, L, R^1, R^2, Y^1, Y^2$ and $Y^3$ are the same as the preferences set out for the corresponding substituents of a compound of formula (I).

Another group of novel intermediates are compounds of formula (XIII)

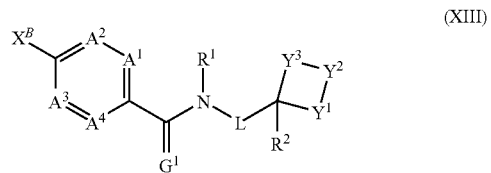

(XIII)

wherein $A^1, A^2, A^3, A^4, G^1, L, R^1, R^2, Y^1, Y^2$ and $Y^3$ are as define formula (I) and $X^B$ is a leaving group, for example a halogen, such as bromo; or a salt or N-oxide thereof. The preferences for $A^1, A^2, A^3, A^4, G^1, L, R^1, R^2, Y^1, Y^2$ and $Y^3$ are the same as the preferences set out for the corresponding substituents of a compound of formula (I).

Another group of novel intermediates are compounds of formula (XIII) wherein $A^1, A^2, A^3, A^4, G^1, L, R^1, R^2, Y^1, Y^2$ and $Y^3$ are as defined for a compound of formula (I) and $X^B$ is a leaving group, for example a halogen, such as bromo; or a salt or N-oxide thereof, provided that the compound is not 3-chloro-4-fluoro-N-{1-[1-(4-methoxy-2,3-dimethyl-phenyl)ethyl]-3-azetidinyl}-benzamide (CAS RN 1005461-02-8), 3-chloro-4-fluoro-N-[{1-[1-(4-methoxy-2,3-dimethylphenyl)ethyl]-3-azetidinyl}methyl]-benzamide (CAS RN 1005471-81-7), 3-chloro-4-fluoro-N-[{1-[1-(4-methoxy-2,3-dimethylphenyl)propyl]-3-azetidinyl}methyl]-benzamide (CAS RN 1005472-44-5), or 3-chloro-4-fluoro-N-[{1-[1-(4-methoxy-2,3-dimethylphenyl)methyl]-3-azetidinyl}methyl]-benzamide (CAS RN 1005472-60-5). The preferences for $A^1, A^2, A^3, A^4, G^1, L, R^1, R^2, Y^1, Y^2$ and $Y^3$ are the same as the preferences set out for the corresponding substituents of a compound of formula (I).

Another group of novel intermediates are compounds of formula (XIII) wherein $A^1, A^2, A^3, A^4, G^1, L, R^1, R^2, Y^1, Y^2$ and $Y^3$ are as defined for a compound of formula (I) and $X^B$ is a leaving group, for example a halogen, such as bromo; or a salt or N-oxide thereof, provided that if one of $Y^1, Y^2$ and $Y^3$ is N—$R^9$, the remaining $Y^1, Y^2$ and $Y^3$ cannot a) both be $CR^7R^8$, or b) be $CR^7R^8$ and C=O, respectively. The preferences for $A^1, A^2, A^3, A^4, G^1, L, R^1, R^2, Y^1, Y^2$ and $Y^3$ are the same as the preferences set out for the corresponding substituents of a compound of formula (I).

Another group of novel intermediates are compounds of formula (XIV)

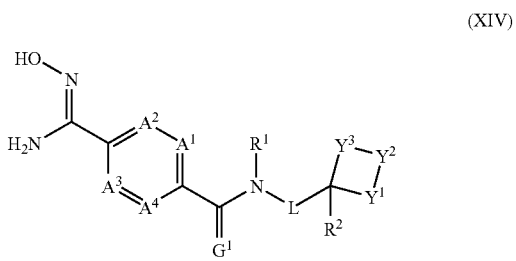

(XIV)

wherein $A^1, A^2, A^3, A^4, G^1, L, R^1, R^2, Y^1, Y^2$ and $Y^3$ are as defined for a compound of formula (I); or a salt or N-oxide thereof. The preferences for $A^1, A^2, A^3, A^4, G^1, L, R^1, R^2, Y^1, Y^2$ and $Y^3$ are the same as the preferences set out for the corresponding substituents of a compound of formula (I).

Another group of novel intermediates are compounds of formula (XV)

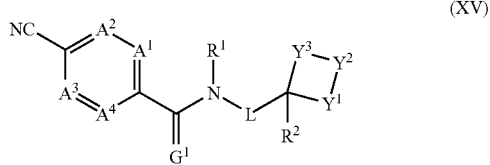
(XV)

wherein $A^1, A^2, A^3, A^4, G^1, L, R^1, R^2, Y^1, Y^2,$ and $Y^3$ are as defined for a compound of formula (I); or a salt or N-oxide thereof. The preferences for $A^1, A^2, A^3, A^4, G^1, L, R^1, R^2, Y^1, Y^2$ and $Y^3$ are the same as the preferences set out for the corresponding substituents of a compound of formula (I).

Another group of novel intermediates are compounds of formula (XVIII)

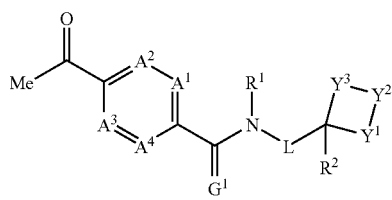
(XVIII)

wherein $A^1, A^2, A^3, A^4, G^1, L, R^1, R^2, Y^1, Y^2$ and $Y^3$ are as defined for a compound of formula (I); or a salt or N-oxide thereof. The preferences for $A^1, A^2, A^3, A^4, L, R^1, R^2, Y^1, Y^2$ and $Y^3$ are the same as the preferences set out for the corresponding substituents of a compound of formula (I).

Another group of novel intermediates are compounds of formula (XIX)

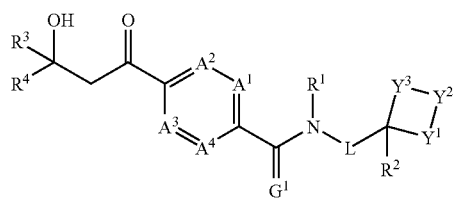
(XIX)

wherein $A^1, A^2, A^3, A^4, L, R^1, R^2, R^3, R^4, Y^1, Y^2$ and $Y^3$ are as defined for a compound of formula (I); or a salt or N-oxide thereof. The preferences for $A^1, A^2, A^3, A^4, G^1, L, R^1, R^2, R^3, R^4, Y^1, Y^2$ and $Y^3$ are the same as the preferences set out for the corresponding substituents of a compound of formula (I).

Another group of novel intermediates are compounds of formula (XX)

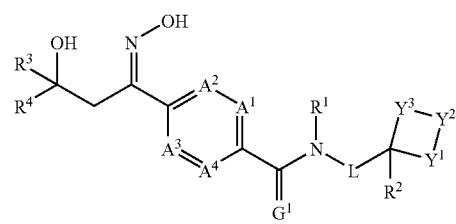
(XX)

wherein $A^1, A^2, A^3, A^4, G^1, L, R^1, R^2, R^3, R^4, Y^1, Y^2$ and $Y^3$ are as defined for a compound of formula (I); or a salt or N-oxide thereof. The preferences for $A^1, A^2, A^3, A^4, G^1, L, R^1, R^2, R^3, R^4, Y^1, Y^2$ and $Y^3$ are the same as the preferences set out for the corresponding substituents of a compound of formula (I).

Another group of novel intermediates are compounds of formula (XXII)

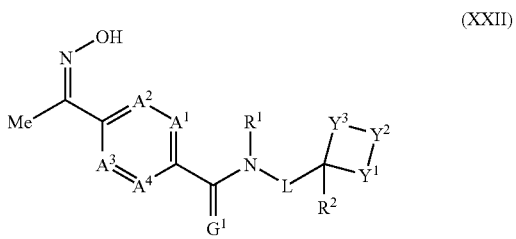
(XXII)

wherein $A^1, A^2, A^3, A^4, L, R^1, R^2, Y^1, Y^2$ and $Y^3$ are as defined for a compound of formula (I); or a salt or N-oxide thereof. The preferences for $A^1, A^2, A^3, A^4, G^1, L, R^1, R^2, Y^1, Y^2$ and $Y^3$ are the same as the preferences set out for the corresponding substituents of a compound of formula (I).

Another group of novel intermediates are compounds of formula (XXIII)

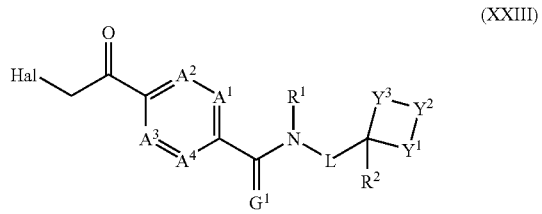
(XXIII)

wherein $A^1, A^2, A^3, A^4, G^1, L, R^1, R^2, Y^1, Y^2$ and $Y^3$ are as defined for a compound of formula (I) and Hal is a halogen, such as bromo or chloro; or a salt or N-oxide thereof. The preferences for $A^1, A^2, A^3, A^4, G^1, L, R^1, R^2, Y^1, Y^2$ and $Y^3$ are the same as the preferences set out for the corresponding substituents of a compound of formula (I).

Another group of novel intermediates are compounds of formula (XXIV)

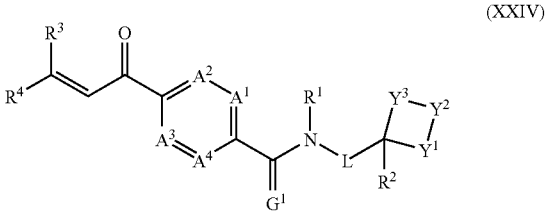
(XXIV)

wherein $A^1, A^2, A^3, A^4, G^1, L, R^1, R^2, R^3, R^4, Y^1, Y^2$ and $Y^3$ are as defined for a compound of formula (I); or a salt or N-oxide thereof. The preferences for $A^1, A^2, A^3, A^4, G^1, L, R^1, R^2, R^3, R^4, Y^1, Y^2$ and $Y^3$ are the same as the preferences set out for the corresponding substituents of a compound of formula (I).

Another group of novel intermediates are compounds of formula (XXIV')

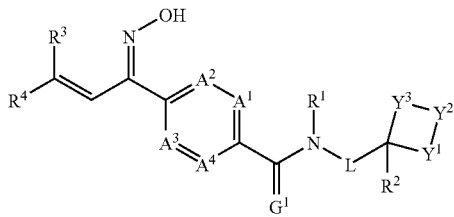

(XXIV')

wherein $A^1, A^2, A^3, A^4, G^1, L, R^1, R^2, R^3, R^4, Y^1, Y^2$ and $Y^3$ are as defined for a compound of formula (I); or a salt or N-oxide thereof. The preferences for $A^1, A^2, A^3, A^4, G^1, L, R^1, R^2, R^3, R^4, Y^1, Y^2$ and $Y^3$ are the same as the preferences set out for the corresponding substituents of a compound of formula (I).

A further embodiment of this invention are compounds of formula (I') wherein $A^1, A^2, A^3$ and $A^4$ are independently of one another C—H, C—$R^5$, or nitrogen; $G^1$ is oxygen or sulfur;

L is a single bond, $C_1$-$C_6$alkyl, $C_1$-$C_6$haloalkyl, $C_2$-$C_6$alkenyl, $C_2$-$C_6$haloalkenyl, $C_2$-$C_6$alkynyl, or $C_2$-$C_6$haloalkynyl;

$R^1$ is hydrogen, $C_1$-$C_6$alkyl, $C_1$-$C_6$alkylcarbonyl, or $C_1$-$C_6$alkoxycarbonyl;

$R^2$ is hydrogen, or $C_1$-$C_6$alkyl;

$R^3$ is $C_1$-$C_6$haloalkyl;

$R^4$ is aryl or aryl substituted by one to three substituents independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl, or heterocyclyl or heterocyclyl substituted by one to three substituents independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl;

each $R^5$ is independently halogen, cyano, nitro, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, or $C_1$-$C_6$alkoxycarbonyl;

$Y^1, Y^2$ and $Y^3$ are independently of another CR$^6$R$^7$, C=O, C=N—OR$^8$, N—R$^8$, S, SO, SO$_2$, S=N—R$^8$, or SO=N—R$^8$, provided that at least one of $Y^1, Y^2$ or $Y^3$ is not CR$^6$R$^7$;

each $R^6$ and $R^7$ is independently hydrogen, halogen, $C_1$-$C_6$alkyl, or $C_1$-$C_6$haloalkyl; and each $R^8$ is independently hydrogen, cyano, $C_1$-$C_6$alkyl, $C_1$-$C_6$haloalkyl, $C_1$-$C_6$alkylcarbonyl, $C_1$-$C_6$haloalkylcarbonyl, $C_1$-$C_6$alkoxycarbonyl, $C_1$-$C_6$haloalkoxycarbonyl, $C_1$-$C_6$alkyl-sulfonyl, $C_1$-$C_6$haloalkylsulfonyl, aryl-$C_1$-$C_4$alkyl-, or aryl-$C_1$-$C_4$alkyl- wherein the aryl moiety is substituted by one to three substituents independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl, heteroaryl-$C_1$-$C_4$alkyl-, or heteroaryl-$C_1$-$C_4$alkyl- wherein the heteroaryl moiety is substituted by one to three substituents independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl; or a salt or N-oxide thereof. The preferences for $A^1, A^2, A^3, A^4, G^1, L, R^1, R^2, R^3, R^4, Y^1, Y^2$ and $Y^3$ are the same as the preferences set out for the corresponding substituents of compounds of the formula (I).

A further embodiment of this invention are compounds of formula (I") wherein $A^1, A^2, A^3$ and $A^4$ are independently of one another C—H, C—$R^5$, or nitrogen;

$G^1$ is oxygen or sulfur;

L is a single bond, $C_1$-$C_8$alkyl, $C_1$-$C_8$haloalkyl, $C_2$-$C_8$alkenyl, $C_2$-$C_8$haloalkenyl, $C_2$-$C_8$alkynyl, or $C_2$-$C_8$haloalkynyl;

$R^1$ is hydrogen, $C_1$-$C_8$alkyl, $C_1$-$C_8$alkylcarbonyl-, or $C_1$-$C_8$alkoxycarbonyl-;

$R^2$ is hydrogen, or $C_1$-$C_8$alkyl;

$R^3$ is $C_1$-$C_8$haloalkyl;

$R^4$ is aryl or aryl substituted by one to three $R^6$, or heterocyclyl or heterocyclyl substituted by one to three $R^6$;

$Y^1, Y^2$ and $Y^3$ are independently of another CR$^7$R$^8$, C=O, C=N—OR$^9$, N—R$^9$, S, SO, SO$_2$, S=N—R$^9$, or SO=N—R$^9$, provided that at least one of $Y^1, Y^2$ or $Y^3$ is not CR$^7$R$^8$;

each $R^5$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, $C_1$-$C_8$alkoxycarbonyl-, aryl or aryl optionally substituted by one to three $R^{10}$, or heteroaryl or heteroaryl optionally substituted by one to three $R^{10}$;

each $R^6$ is independently halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl-;

each $R^7$ and $R^8$ is independently hydrogen, halogen, $C_1$-$C_8$alkyl, or $C_1$-$C_8$haloalkyl;

each $R^9$ is independently hydrogen, cyano, $C_1$-$C_8$alkyl, $C_1$-$C_8$haloalkyl, $C_1$-$C_8$alkylcarbonyl-, $C_1$-$C_8$haloalkylcarbonyl-, $C_1$-$C_8$alkoxycarbonyl-, $C_1$-$C_8$haloalkoxycarbonyl-, $C_1$-$C_8$alkyl-sulfonyl-, $C_1$-$C_8$haloalkylsulfonyl-, aryl-$C_1$-$C_4$alkyl- or aryl-$C_1$-$C_4$alkyl- wherein the aryl moiety is substituted by one to three $R^{11}$, or heteroaryl-$C_1$-$C_4$alkyl- or heteroaryl-$C_1$-$C_4$alkyl- wherein the heteroaryl moiety is substituted by one to three $R^{11}$;

each $R^{10}$ is independently halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl-; and each $R^{11}$ is independently halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl-; or a salt or N-oxide thereof. The preferences for $A^1, A^2, A^3, A^4, L, R^1, R^2, R^3, R^4, Y^1, Y^2$ and $Y^3$ are the same as preferences set out for the corresponding substituents of compounds of the formula (I).

The compounds in Table 1 to Table 32 below illustrate the compounds of the invention.

Table 1:

Table 1 provides 8 compounds of formula (Ia) wherein $G^1$ is oxygen, $R^1$ is hydrogen, $R^5$ is bromo, $Y^2$ is C=O, and $R^2$, $Y^1$ and $Y^3$ have the values listed in the table below.

(Ia)

[Chemical structure of formula (Ia)]

| Compound numbers | $R^2$ | $Y^1$ | $Y^3$ |
|---|---|---|---|
| 1.01 | H | $CH_2$ | $CH_2$ |
| 1.02 | H | CH(Me) | $CH_2$ |
| 1.03 | H | $C(Me)_2$ | $CH_2$ |
| 1.04 | H | $C(Me)_2$ | $C(Me)_2$ |
| 1.05 | Me | $CH_2$ | $CH_2$ |
| 1.06 | Me | CH(Me) | $CH_2$ |
| 1.07 | Me | $C(Me)_2$ | $CH_2$ |
| 1.08 | Me | $C(Me)_2$ | $C(Me)_2$ |

Table 2:
Table 2 provides 8 compounds of formula (Ia) wherein $G^1$ is oxygen, $R^1$ is hydrogen, $R^5$ is bromo, $Y^2$ is C=N—OMe, and $R^2$, $Y^1$ and $Y^3$ have the values listed in Table 1.

Table 3:
Table 3 provides 8 compounds of formula (Ia) wherein $G^1$ is oxygen, $R^1$ is hydrogen, $R^5$ is bromo, $Y^2$ is N-Me, and $R^2$, $Y^1$ and $Y^3$ have the values listed in Table 1.

Table 4:
Table 4 provides 8 compounds of formula (Ia) wherein $G^1$ is oxygen, $R^1$ is hydrogen, $R^5$ is bromo, $Y^2$ is N—$CH_2$—$C_6H_5$, and $R^2$, $Y^1$ and $Y^3$ have the values listed in Table 1.

Table 5:
Table 5 provides 8 compounds of formula (Ia) wherein $G^1$ is oxygen, $R^1$ is hydrogen, $R^5$ is bromo, $Y^2$ is S, and $R^2$, $Y^1$ and $Y^3$ have the values listed in Table 1.

Table 6:
Table 6 provides 8 compounds of formula (Ia) wherein $G^1$ is oxygen, $R^1$ is hydrogen, $R^5$ is bromo, $Y^2$ is SO, and $R^2$, $Y^1$ and $Y^3$ have the values listed in Table 1.

Table 7:
Table 7 provides 8 compounds of formula (Ia) wherein $G^1$ is oxygen, $R^1$ is hydrogen, $R^5$ is bromo, $Y^2$ is $SO_2$, and $R^2$, $Y^1$ and $Y^3$ have the values listed in Table 1.

Table 8:
Table 8 provides 8 compounds of formula (Ia) wherein $G^1$ is oxygen, $R^1$ is hydrogen, $R^5$ is bromo, $Y^2$ is SONH, and $R^2$, $Y^1$ and $Y^3$ have the values listed in Table 1.

Table 9:
Table 9 provides 8 compounds of formula (Ia) wherein $G^1$ is oxygen, $R^1$ is hydrogen, $R^5$ is cyano, $Y^2$ is C=O, and $R^2$, $Y^1$ and $Y^3$ have the values listed in Table 1.

Table 10:
Table 10 provides 8 compounds of formula (Ia) wherein $G^1$ is oxygen, $R^1$ is hydrogen, $R^5$ is cyano, $Y^2$ is C=N—OMe, and $R^2$, $Y^1$ and $Y^3$ have the values listed in Table 1.

Table 11:
Table 11 provides 8 compounds of formula (Ia) wherein $G^1$ is oxygen, $R^1$ is hydrogen, $R^5$ is cyano, $Y^2$ is N-Me, and $R^2$, $Y^1$ and $Y^3$ have the values listed in Table 1.

Table 12:
Table 12 provides 8 compounds of formula (Ia) wherein $G^1$ is oxygen, $R^1$ is hydrogen, $R^5$ is cyano, $Y^2$ is N—$CH_2$—$C_6H_5$, and $R^2$, $Y^1$ and $Y^3$ have the values listed in Table 1.

Table 13:
Table 13 provides 8 compounds of formula (Ia) wherein $G^1$ is oxygen, $R^1$ is hydrogen, $R^5$ is cyano, $Y^2$ is S, and $R^2$, $Y^1$ and $Y^3$ have the values listed in Table 1.

Table 14:
Table 14 provides 8 compounds of formula (Ia) wherein $G^1$ is oxygen, $R^1$ is hydrogen, $R^5$ is cyano, $Y^2$ is SO, and $R^2$, $Y^1$ and $Y^3$ have the values listed in Table 1.

Table 15:
Table 15 provides 8 compounds of formula (Ia) wherein $G^1$ is oxygen, $R^1$ is hydrogen, $R^5$ is cyano, $Y^2$ is $SO_2$, and $R^2$, $Y^1$ and $Y^3$ have the values listed in Table 1.

Table 16:
Table 16 provides 8 compounds of formula (Ia) wherein $G^1$ is oxygen, $R^1$ is hydrogen, $R^5$ is cyano, $Y^2$ is SONH, and $R^2$, $Y^1$ and $Y^3$ have the values listed in Table 1.

Table 17:
Table 17 provides 8 compounds of formula (Ia) wherein $G^1$ is oxygen, $R^1$ is hydrogen, $R^5$ is methyl, $Y^2$ is C=O, and $R^2$, $Y^1$ and $Y^3$ have the values listed in Table 1.

Table 18:
Table 18 provides 8 compounds of formula (Ia) wherein $G^1$ is oxygen, $R^1$ is hydrogen, $R^5$ is methyl, $Y^2$ is C=N—OMe, and $R^2$, $Y^1$ and $Y^3$ have the values listed in Table 1.

Table 19:
Table 19 provides 8 compounds of formula (Ia) wherein $G^1$ is oxygen, $R^1$ is hydrogen, $R^5$ is methyl, $Y^2$ is N-Me, and $R^2$, $Y^1$ and $Y^3$ have the values listed in Table 1.

Table 20:
Table 20 provides 8 compounds of formula (Ia) wherein $G^1$ is oxygen, $R^1$ is hydrogen, $R^5$ is methyl, $Y^2$ is N—$CH_2$—$C_6H_5$, and $R^2$, $Y^1$ and $Y^3$ have the values listed in Table 1.

Table 21:
Table 21 provides 8 compounds of formula (Ia) wherein $G^1$ is oxygen, $R^1$ is hydrogen, $R^5$ is methyl, $Y^2$ is S, and $R^2$, $Y^1$ and $Y^3$ have the values listed in Table 1.

Table 22:
Table 22 provides 8 compounds of formula (Ia) wherein $G^1$ is oxygen, $R^1$ is hydrogen, $R^5$ is methyl, $Y^2$ is SO, and $R^2$, $Y^1$ and $Y^3$ have the values listed in Table 1.

Table 23:
Table 23 provides 8 compounds of formula (Ia) wherein $G^1$ is oxygen, $R^1$ is hydrogen, $R^5$ is methyl, $Y^2$ is $SO_2$, and $R^2$, $Y^1$ and $Y^3$ have the values listed in Table 1.

Table 24:
Table 24 provides 8 compounds of formula (Ia) wherein $G^1$ is oxygen, $R^1$ is hydrogen, $R^5$ is methyl, $Y^2$ is SONH, and $R^2$, $Y^1$ and $Y^3$ have the values listed in Table 1.

Table 25:
Table 25 provides 8 compounds of formula (Ia) wherein $G^1$ is oxygen, $R^1$ is hydrogen, $R^5$ is trifluoromethyl, $Y^2$ is C=O, and $R^2$, $Y^1$ and $Y^3$ have the values listed in Table 1.

Table 26:
Table 26 provides 8 compounds of formula (Ia) wherein $G^1$ is oxygen, $R^1$ is hydrogen, $R^5$ is trifluoromethyl, $Y^2$ is C=N—OMe, and $R^2$, $Y^1$ and $Y^3$ have the values listed in Table 1.

Table 27:
Table 27 provides 8 compounds of formula (Ia) wherein $G^1$ is oxygen, $R^1$ is hydrogen, $R^5$ is trifluoromethyl, $Y^2$ is N-Me, and $R^2$, $Y^1$ and $Y^3$ have the values listed in Table 1.

Table 28:
Table 28 provides 8 compounds of formula (Ia) wherein $G^1$ is oxygen, $R^1$ is hydrogen, $R^5$ is trifluoromethyl, $Y^2$ is N—$CH_2$—$C_6H_5$, and $R^2$, $Y^1$ and $Y^3$ have the values listed in Table 1.

Table 29:

Table 29 provides 8 compounds of formula (Ia) wherein $G^1$ is oxygen, $R^1$ is hydrogen, $R^5$ is trifluoromethyl, $Y^2$ is S, and $R^2$, $Y^1$ and $Y^3$ have the values listed in Table 1.

Table 30:

Table 30 provides 8 compounds of formula (Ia) wherein $G^1$ is oxygen, $R^1$ is hydrogen, $R^5$ is trifluoromethyl, $Y^2$ is SO, and $R^2$, $Y^1$ and $Y^3$ have the values listed in Table 1.

Table 31:

Table 31 provides 8 compounds of formula (Ia) wherein $G^1$ is oxygen, $R^1$ is hydrogen, $R^5$ is trifluoromethyl, $Y^2$ is $SO_2$, and $R^2$, $Y^1$ and $Y^3$ have the values listed in Table 1.

Table 32:

Table 32 provides 8 compounds of formula (Ia) wherein $G^1$ is oxygen, $R^1$ is hydrogen, $R^5$ is trifluoromethyl, $Y^2$ is SONH, and $R^2$, $Y^1$ and $Y^3$ have the values listed in Table 1.

The compounds of the invention may be made by a variety of methods as shown in Schemes 1 to 7.

("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a tempera-

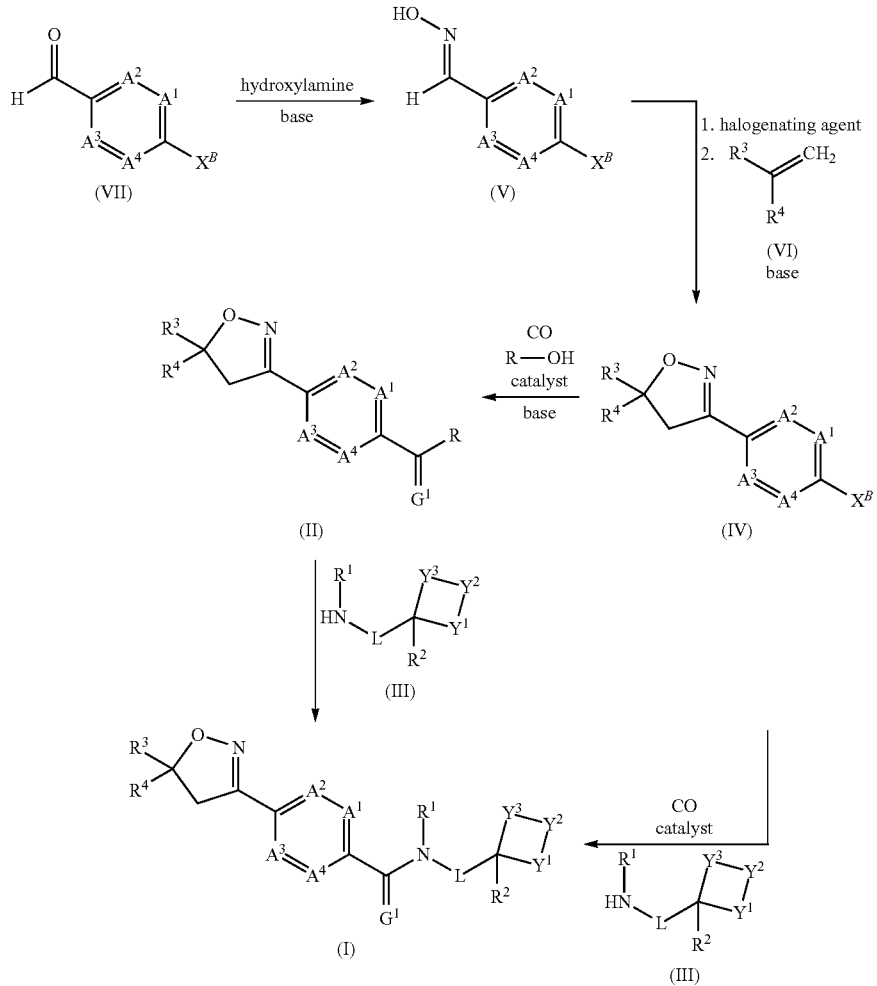

Scheme 1

1) Compounds of formula (I) wherein $G^1$ is oxygen, can be prepared by reacting a compound of formula (II) wherein $G^1$ is oxygen and R is OH, $C_1$-$C_6$alkoxy or Cl, F or Br, with an amine of formula (III) as shown in Scheme 1. When R is OH such reactions are usually carried out in the presence of a coupling reagent, such as N,N'-dicyclohexylcarbodiimide ture of from 0° C. to 100° C., preferably from 15° C. to 30° C., in particular at ambient temperature. Amines of formula (III) are known in the literature or can be prepared using methods known to a person skilled in the art.

2) Acid halides of formula (II), wherein $G^1$ is oxygen and R is Cl, F or Br, may be made from carboxylic acids of formula (II), wherein G¹ is oxygen and R is OH, under standard conditions, such as treatment with thionyl chloride or oxalyl chloride. A preferred solvent is dichloromethane. The reaction is carried out at a temperature of from 0° C. to 100° C., preferably from 15° C. to 30° C., in particular at ambient temperature.

3) Carboxylic acids of formula (II), wherein G¹ is oxygen and R is OH, may be formed from esters of formula (II), wherein G¹ is oxygen and R is $C_1$-$C_6$alkoxy. It is known to a person skilled in the art that there are many methods for the hydrolysis of such esters depending on the nature of the alkoxy group. One widely used method to achieve such a transformation is the treatment of the ester with an alkali hydroxide, such as lithium hydroxide, sodium hydroxide or potassium hydroxide, in a solvent, such as ethanol or tetrahydrofuran, in the presence of water. Another is the treatment of the ester with an acid, such as trifluoroacetic acid, in a solvent, such as dichloromethane, followed by addition of water. The reaction is carried out at a temperature of from 0° C. to 150° C., preferably from 15° C. to 100° C., in particular at 50° C.

4) Compounds of formula (II) wherein G¹ is oxygen and R is $C_1$-$C_6$alkoxy, can be prepared by reacting a compound of formula (IV) wherein $X^B$ is a leaving group, for example a halogen, such as bromo, with carbon monoxide and an alcohol of formula R—OH; such as ethanol, in the presence of a catalyst, such as bis(triphenylphosphine)palladium(II) dichloride, and a base, such as pyridine, triethylamine, 4-(dimethylamino)-pyridine ("DMAP") or diisopropylethylamine (Hunig's base). The reaction is carried out at a temperature of from 50° C. to 200° C., preferably from 100° C. to 150° C., in particular at 115° C. The reaction is carried out at a pressure of from 50 to 200 bar, preferably from 100 to 150 bar, in particular at 120 bar.

5) Alternatively, compounds of formula (I) wherein G¹ is oxygen, can be prepared by reacting a compound of formula (IV) wherein $X^B$ is a leaving group, for example a halogen, such as bromo, with carbon monoxide and an amine of formula (III), in the presence of a catalyst, such as palladium(II) acetate or bis(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

6) Compounds of formula (IV) wherein $X^B$ is a leaving group, for example a halogen, such as bromo, can be made by reaction of an oxime of formula (V) wherein $X^B$ is a leaving group, for example a halogen, such as bromo, and a vinyl compound of formula (VI) in a two step reaction. In the first step, the oxime of formula (V) is reacted with a halogenating agent, for example a succinimide, such as N-chlorosuccinimide ("NCS"), in the presence of a suitable solvent, for example a polar solvent, such as N,N-dimethylformamide. The first step is carried out at a temperature of from 0° C. to 100° C., preferably from 15° C. to 30° C., in particular at ambient temperature.

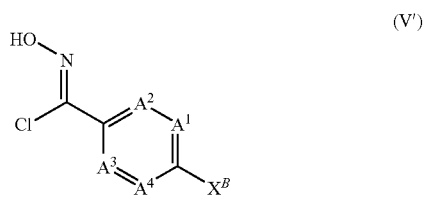

In the second step, the chloro hydroxy imine intermediate of formula (V') is reacted with the vinyl compound of formula (VI) in the presence of a base, for example an organic base, such as triethylamine, or an inorganic base, such as sodium hydrogen carbonate, in the presence of a suitable solvent, for example a polar solvent, such as N,N-dimethylformamide or isopropanol. It is possible to conduct these two steps separately and optionally to isolate the chloro hydroxy imine intermediate (see Example I12 and Example I13) or more conveniently to conduct these two steps successively in one reaction vessel without isolation of the intermediate (see Example I3). The second step is carried out at a temperature of from 0° C. to 100° C., preferably from 15° C. to 30° C., in particular at ambient temperature. Vinyl compounds of formula (VI) are commercially available or can be made by methods known to a person skilled in the art.

7) Compounds of formula (V) wherein $X^B$ is a leaving group, for example a halogen, such as bromo, can be made by reaction of an aldehyde of formula (VII) wherein $X^B$ is a leaving group, for example a halogen, such as bromo, with a hydroxylamine, such as hydroxylamine hydrochloride. Such reactions are carried out in the presence of a base, for example an organic base, such as triethylamine or sodium acetate, or an inorganic base, such as sodium hydrogen carbonate, optionally in the presence of a solvent, for example an alcohol, such as methanol or ethanol, or water, or mixtures thereof. The reaction is carried out at a temperature of from 0° C. to 100° C., preferably from 15° C. to 30° C., in particular at ambient temperature. Aldehydes of formula (VII) are commercially available or can be made by methods known to a person skilled in the art.

8) Compounds of formula (I) wherein G¹ is oxygen and one of $Y^1$, $Y^2$ and $Y^3$ is SO or $SO_2$ and the remaining $Y^1$, $Y^2$ and $Y^3$ are independently $CR^7R^8$, can be made from a compound of formula (I) wherein G¹ is oxygen and one of $Y^1$, $Y^2$ and $Y^3$ is S (or SO) and the remaining $Y^1$, $Y^2$ and $Y^3$ are independently $CR^7R^8$, by treatment with an oxidising reagent, such as potassium permanganate, 3-chloroperoxybenzoic acid ("MCPBA"), sodium periodate/ruthenium(II) oxide, hydrogen peroxide, oxone and sodium hypochlorite. One equivalent of oxidising reagent is required to convent a sulfide to a sulfoxide, or a sulfoxide to a sulfone. Two equivalents of oxidising reagent are required to convent a sulfide to a sulfone. Preferred solvents are tetrahydrofuran, dioxane, 1,2-dimethoxyethane, ethyl acetate, toluene, dichloromethane and water, or mixtures thereof. The reaction is optionally carried out in the presence of a base, for example a carbonate, such as sodium hydrogen carbonate. The reaction is carried out at a temperature of from 0° C. to 100° C., preferably from 15° C. to 30° C., in particular at ambient temperature. Alternatively, these transformations can be carried out on an amine of formula (III) or on a protected form of an amine of formula (III). For protecting groups suitable for amines, see, for example, Greene's Protective Groups in Organic Synthesis, 4th Edition, P. G. M. Wuts, T. W. Greene, October 2006.

9) Compounds of formula (I) wherein G¹ is oxygen and one of $Y^1$, $Y^2$ and $Y^3$ is SO=N—$R^9$ and the remaining $Y^1$, $Y^2$ and $Y^3$ are independently $CR^7R^8$, can be made from a compound of formula (I) wherein $G^1$ is oxygen and one of $Y^1$, $Y^2$ and $Y^3$ is S=N—$R^9$ and the remaining $Y^1$, $Y^2$ and $Y^3$ are independently $CR^7R^8$, by treatment with an oxidising reagent, such as potassium permanganate, 3-chloroperoxybenzoic acid ("MCPBA"), sodium periodate/ruthenium(II) oxide, hydrogen peroxide, oxone and sodium hypochlorite. One equivalent of oxidising reagent is required to convent a sulfilimine to a sulfoximine. Preferred solvents are tetrahydrofuran, dioxane, 1,2-dimethoxyethane, ethyl acetate, toluene, dichloromethane and water, or mixtures thereof. The reaction is optionally carried out in the presence of a base, for example a carbonate, such as sodium hydrogen carbonate. The reaction is carried out at a temperature of from 0° C. to 100° C., preferably from 15° C. to 30° C., in particular at ambient temperature. Alternatively, this transformation can be carried out on an amine of formula (III) or on a protected form of an amine of formula (III). For protecting groups suitable for amines, see, for example, Greene's Protective Groups in Organic Synthesis, 4th Edition, P. G. M. Wuts, T. W. Greene, October 2006.

10) Compounds of formula (I) wherein $G^1$ is oxygen and one of $Y^1$, $Y^2$ and $Y^3$ is S=N—$R^9$ or SO=N—$R^9$ and the remaining $Y^1$, $Y^2$ and $Y^3$ are independently $CR^7R^8$, can be made from a compound of formula (I) wherein $G^1$ is oxygen and one of $Y^1$, $Y^2$ and $Y^3$ is S or SO, respectively, and the remaining $Y^1$, $Y^2$ and $Y^3$ are independently $CR^7R^8$, by treatment with a reagent, such as sodium azide in sulfuric acid, O-mesitylenesulfonylhydroxylamine ("MSH"), or metal-catalyzed methods such as $R^9N_3$/$FeCl_2$, PhI=N—$R^9$/CuOTf, PhI=N—$R^9$/Cu(OTf)$_2$, PhI=N—$R^9$/CuPF$_6$, PhI(OAc)$_2$/$R^9$—NH$_2$/MgO/Rh$_2$(OAc)$_4$ or oxaziridines (e.g. 3-(4-cyano-phenyl)-oxaziridine-2-carboxylic acid tert-butyl ester). One equivalent of reagent is required to convert a sulfoxide to a sulfoximine, or a sulfide to a sulfilimine. Alternatively, these transformations can be carried out on an amine of formula (III) or on a protected form of an amine of formula (III). For protecting groups suitable for amines, see, for example, Greene's Protective Groups in Organic Synthesis, 4th Edition, P. G. M. Wuts, T. W. Greene, October 2006.

11) Compounds of formula (I), wherein $G^1$ is sulfur, may be made by treatment of a compound of formula (II), wherein $G^1$ is oxygen and R is OH, $C_1$-$C_6$alkoxy or Cl, F or Br, with a thio-transfer reagent such as Lawesson's reagent or phosphorus pentasulfide prior to elaborating to compounds of formula (I), as described under 1).

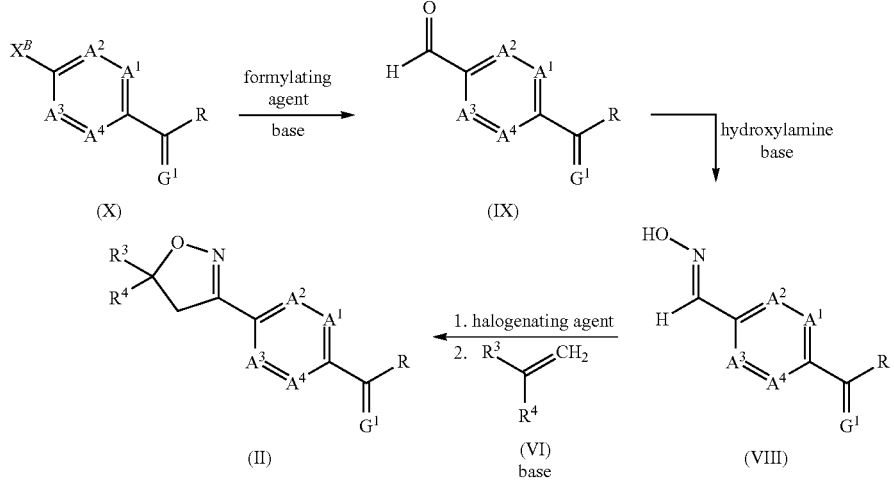

Scheme 2

12) Alternatively, compounds of formula (II) wherein $G^1$ is oxygen and R is $C_1$-$C_6$alkoxy, such as methoxy or tert-butoxy, can be prepared by reaction of an oxime of formula (VIII) wherein $G^1$ is oxygen and R is $C_1$-$C_6$alkoxy, such as methoxy or tert-butoxy, with a halogenating agent followed by a vinyl compound of formula (VI) and base as shown in Scheme 2 in a two step reaction as described under 6). The intermediate of formula (VIII') wherein $G^1$ is oxygen and R is $C_1$-$C_6$alkoxy, such as methoxy or tert-butoxy, can optionally be isolated (see Example I12).

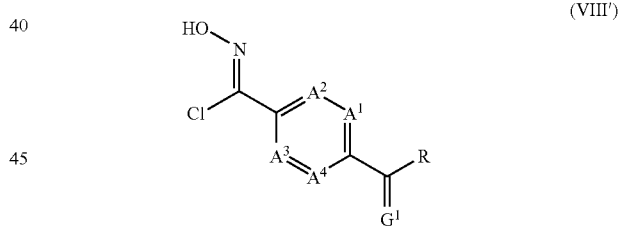

13) Compounds of formula (VIII) wherein $G^1$ is oxygen and R is $C_1$-$C_6$alkoxy, such as methoxy or tert-butoxy, can be made by reaction of an aldehyde of formula (IX) wherein $G^1$ is oxygen and R is $C_1$-$C_6$alkoxy, for example methoxy or tert-butoxy, with a hydroxylamine, such as hydroxylamine hydrochloride, as described under 7).

14) Compounds of formula (IX) wherein $G^1$ is oxygen and R is $C_1$-$C_6$alkoxy, such as methoxy or tert-butoxy, can be prepared by reaction of a compound of formula (X) wherein $G^1$ is oxygen and R is $C_1$-$C_6$alkoxy, for example methoxy or tert-butoxy, and $X^B$ is a leaving group, for example a halogen, such as bromo, with a formylating agent, such as N,N-dimethylformamide. Such reactions are carried out in the presence of a base, for example a lithium base, such as n-butyl lithium, in the presence of a suitable solvent, for example a polar solvent, such as tetrahydrofuran or excess N,N-dimethylformamide. Compounds of formula (X) wherein $G^1$ is oxygen and R is $C_1$-$C_6$alkoxy, such as methoxy or tert-butoxy, are commercially available or can be made by methods known to a person skilled in the art.

Scheme 3

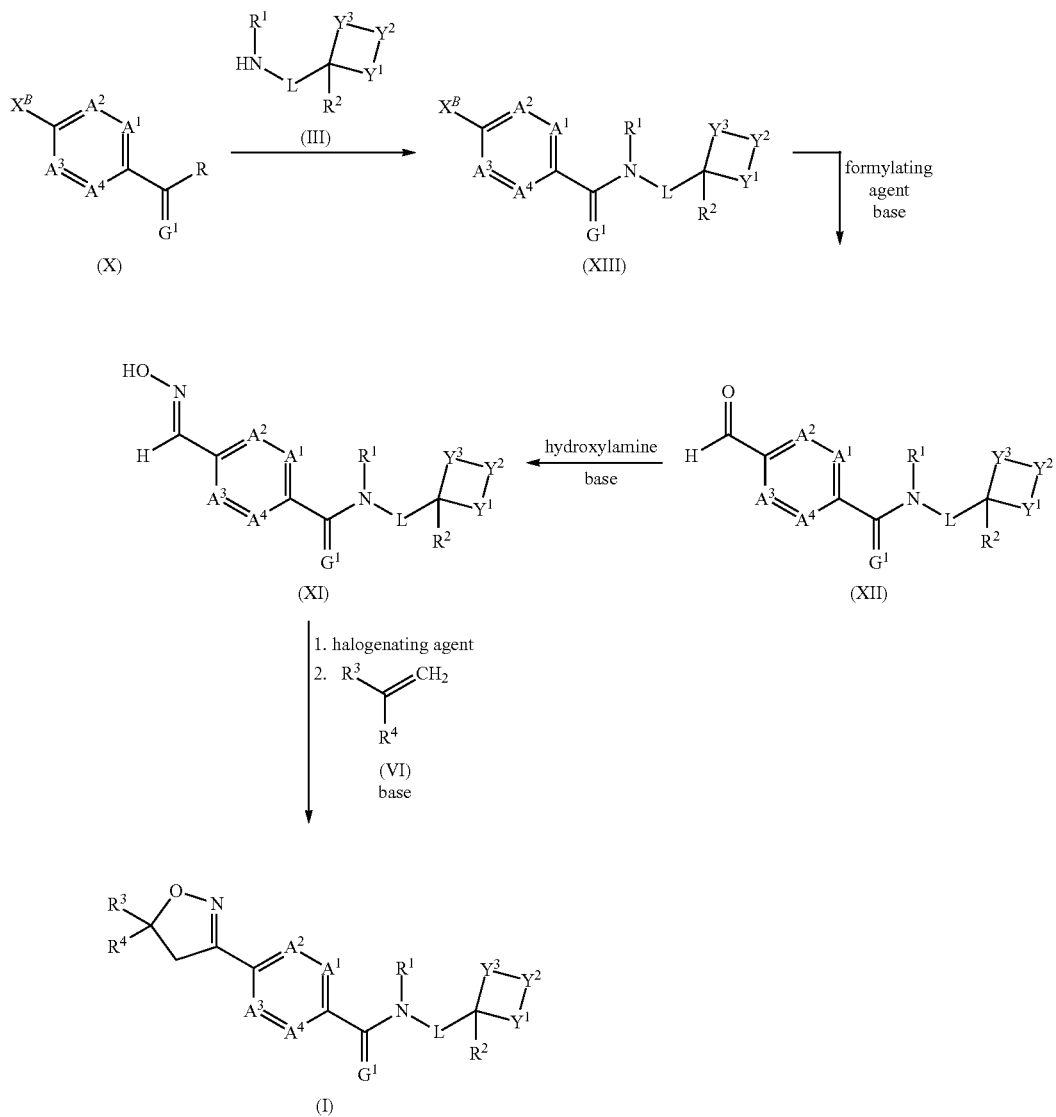

15) Alternatively, compounds of formula (I) wherein $G^1$ is oxygen, can be prepared by reaction of an oxime of formula (XI) wherein $G^1$ is oxygen, with a halogenating agent followed by a vinyl compound of formula (VI) and base as shown in Scheme 3 in a two step reaction as described under 6). The intermediate of formula (XI') wherein $G^1$ is oxygen, can optionally be isolated.

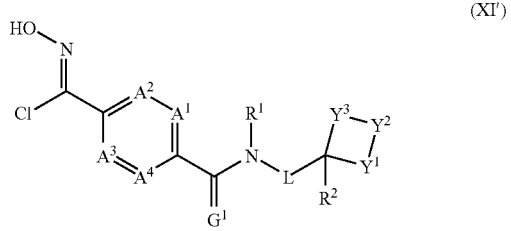

(XI')

16) Compounds of formula (XI) wherein $G^1$ is oxygen, can be made by reaction of an aldehyde of formula (XII) wherein $G^1$ is oxygen, with a hydroxylamine, such as hydroxylamine hydrochloride as described under 7).

17) Compounds of formula (XII) wherein $G^1$ is oxygen, can be prepared by reaction of a compound of formula (XIII) wherein $G^1$ is oxygen and $X^B$ is a leaving group, for example a halogen, such as bromo, with a formylating agent, such as N,N-dimethylformamide as described under 13).

18) Compounds of formula (XIII) wherein $G^1$ is oxygen and $X^B$ is a leaving group, for example a halogen, such as bromo, can be prepared by reacting an acid derivative of formula (X) wherein $G^1$ is oxygen and R is OH, $C_1$-$C_6$alkoxy or Cl, F or Br, and $X^B$ is a leaving group, for example a halogen, such as bromo, with an amine of formula (III) as described under 1).

Scheme 4

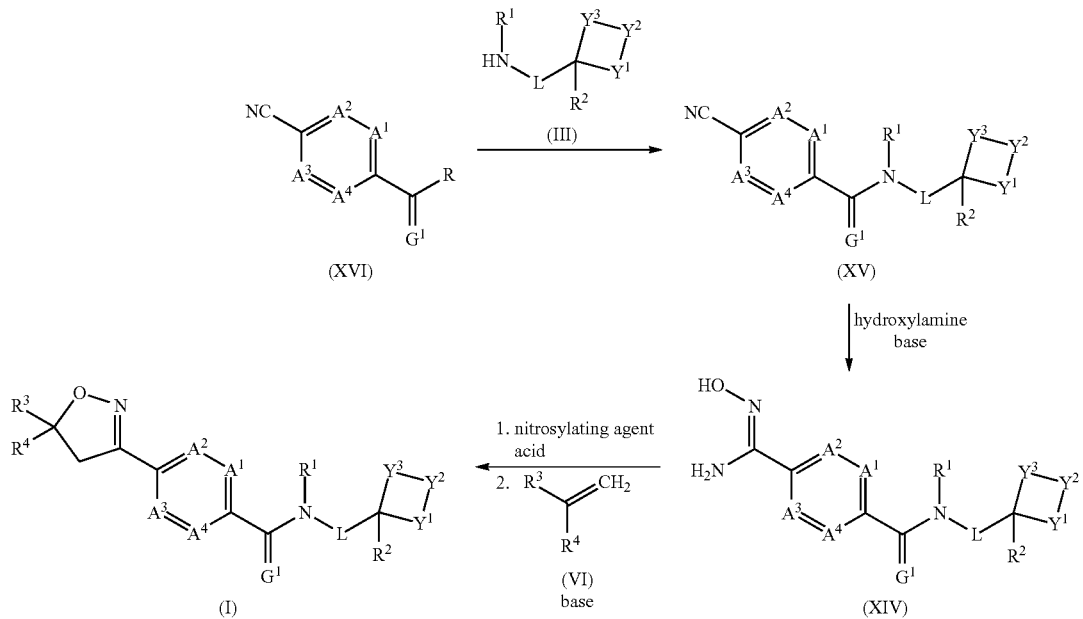

19) Alternatively, compounds of formula (I) wherein $G^1$ is oxygen, can be made by reaction of an N-hydroxy-amidine of formula (XIV) wherein $G^1$ is oxygen, and a vinyl compound of formula (VI) in a two step reaction as shown in Scheme 4. In the first step, the N-hydroxy-amidine of formula (XIV) wherein $G^1$ is oxygen, is reacted with a nitrosylating agent, such as sodium nitrite, in the presence of an acid, such as aqueous hydrochloric acid. The first step is carried out at a temperature of from −20° C. to +30° C., preferably from −5° C. to +10° C.

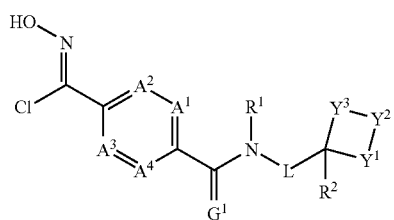

In the second step, the chloro hydroxy imine intermediate of formula (XI') wherein $G^1$ is oxygen, is reacted with the vinyl compound of formula (VI) in the presence of a base, for example an organic base, such as triethylamine, or an inorganic base, such as sodium hydrogen carbonate, in the presence of a suitable solvent, for example a polar solvent, such as N,N-dimethylformamide or isopropanol. It is possible to conduct these two steps separately and optionally to isolate the chloro hydroxy imine intermediate or more conveniently to conduct these two steps successively in one reaction vessel without isolation of the intermediate. The second step is carried out at a temperature of from 0° C. to 100° C., preferably from 15° C. to 30° C., in particular at ambient temperature.

20) Compounds of formula (XIV) wherein $G^1$ is oxygen, can be made by reaction of a nitrile of formula (XV) wherein $G^1$ is oxygen, with a hydroxylamine, such as hydroxylamine hydrochloride as described under 7).

21) Compounds of formula (XV) wherein $G^1$ is oxygen, can be prepared by reacting an acid derivative of formula (XVI) wherein $G^1$ is oxygen and R is OH, $C_1$-$C_6$alkoxy or Cl, F or Br, with an amine of formula (III) as described under 1). Compounds of formula (XVI) wherein $G^1$ is oxygen and R is $C_1$-$C_6$alkoxy, such as methoxy or tert-butoxy, are commercially available or can be made by methods known to a person skilled in the art. Alternatively, compounds of formula (XV) wherein $G^1$ is oxygen, can be prepared by displacing a leaving group of a compound of formula (XII) wherein $G^1$ is oxygen, with a cyano group.

Scheme 5

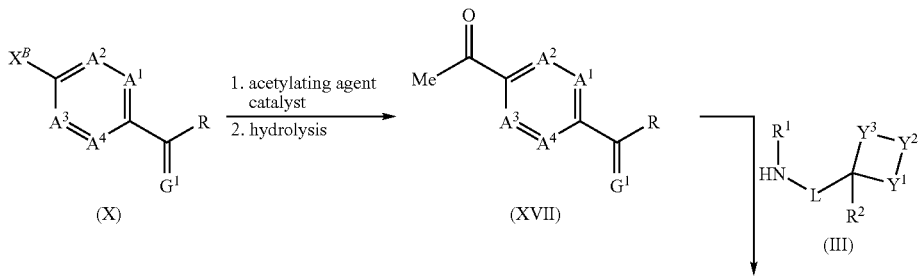

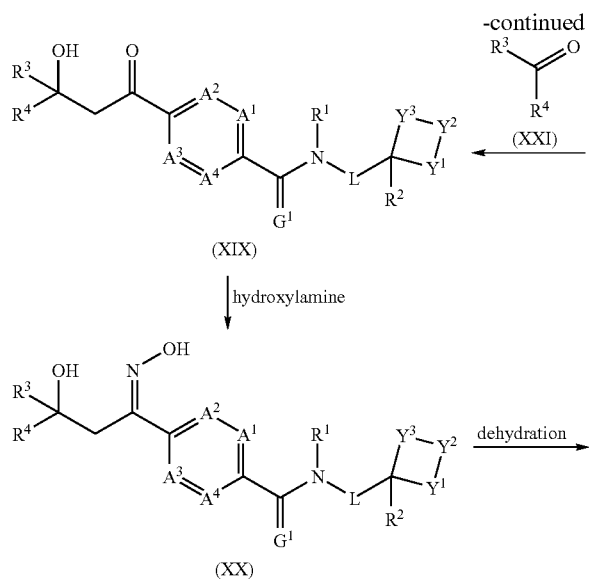

(XIX)

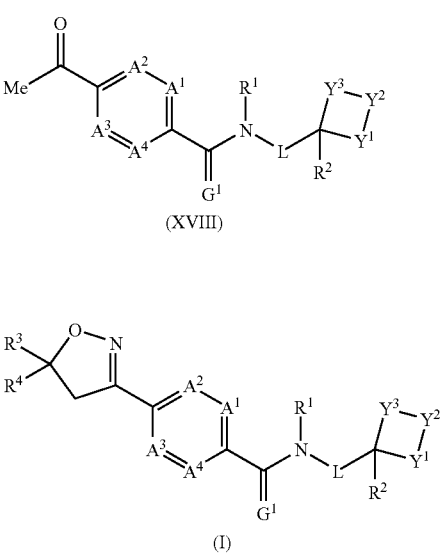

(XVIII)

hydroxylamine ↓ dehydration →

(XX)   (I)

22) Alternatively, compounds of formula (I) wherein $G^1$ is oxygen, can be prepared by cyclisation of a compound of formula (XX) wherein $G^1$ is oxygen, as shown in Scheme 5. The cyclisation of a compound of formula (XX) can also be referred to as the dehydration of a compound of formula (XX). Such reactions are usually carried out in the presence of an acid, for example an inorganic acid, such as hydrochloric acid or sulfuric acid, or a sulfonic acid, such as methanesulfonic acid, optionally in a solvent such as water, ethanol or tetrahydrofuran, or mixtures thereof. The reaction is carried out at a temperature of from 0° C. to 100° C., preferably from 40° C. to 80° C. Representative experimental conditions for this transformation are described in Synthetic Communications 2003, 23, 4163-4171. Alternatively, dehydration can be carried out using a dehydrating agent, such as phosphorus pentoxide, in a solvent, such as chloroform, at a temperature of –20° C. to +50°, preferably at 0° C., as described in Journal of Heterocyclic Chemistry 1990, 27, 275. Alternatively, cyclisation can be carried out under Mitsunobu conditions involving treatment of a compound of formula (XX) with a phosphine, such as triphenylphosphine, and an azodicarboxylate reagent, such as diethyl azodicarboxylate, diisopropyl azodicarboxylate or dicyclohexyl azodicarboxylate, in a solvent, such as tetrahydrofuran, at a temperature of from 0° C. to 80° C., preferably from 0° C. to ambient temperature.

23) Compounds of formula (XX) wherein $G^1$ is oxygen, can be made by reaction of a β-hydroxy ketone of formula (XIX) wherein $G^1$ is oxygen, with a hydroxylamine, such as hydroxylamine hydrochloride. Such reactions are carried out optionally in the presence of a base, for example an organic base, such as triethylamine or sodium acetate, or an inorganic base, such as sodium hydrogen carbonate, optionally in the presence of a solvent, for example an alcohol, such as methanol or ethanol, or water, or mixtures thereof. The reaction is carried out at a temperature of from 0° C. to 100° C., preferably from 15° C. to 30° C., in particular at ambient temperature.

24) Compounds of formula (XIX) wherein $G^1$ is oxygen, can be made by aldol-type reaction of a methyl ketone of formula (XVIII) wherein $G^1$ is oxygen, with a ketone of formula (XXI). Such reactions are usually carried out in the presence of a base, such as sodium hydride, lithium hydride, lithium diisopropylamide or lithium hexamethyldisilazide, in a solvent, such as tetrahydrofuran, at a temperature of from –78° C. to +100° C., preferably from 0° C. to +80° C. Alternatively, the reaction can be performed using a Lewis acid, such as titanium tetrachloride, and an amine, such as triethylamine, diisopropylethylamine, tetramethylethylenediamine ("TMEDA") or tributylamine, in a solvent, such as dichloromethane, at a temperature of from –78° C. to ambient temperature, preferably at –78° C. Representative conditions for such a transformation are given in Tetrahedron Letters 1997, 38, 8727-8730. Ketones of formula (XXI) are commercially available or can be made by methods known to a person skilled in the art.

25) Compounds of formula (XVIII) wherein $G^1$ is oxygen, can be made by reacting an acid derivative of formula (XVII) wherein $G^1$ is oxygen and R is OH, $C_1$-$C_6$alkoxy or Cl, F or Br, with an amine of formula (III) as described under 1).

26) Compounds of formula (XVII) wherein $G^1$ is oxygen and R is $C_1$-$C_6$alkoxy, can be prepared by reacting a compound of formula (X) wherein $G^1$ is oxygen and $X^B$ is a leaving group, for example a halogen, such as bromo, with an acetylating reagent, such as tributyl(1-ethoxyvinyl)tin, ethyl vinyl ether or butyl vinyl ether, in a presence of a catalyst, such as palladium(0) tetrakis(triphenylphosphine), in a solvent, such as tetrahydrofuran or toluene, at a temperature of from 60° C. to 110° C. The reaction may afford an intermediate of formula (XVII') wherein $G^1$ is oxygen and R' is $C_1$-$C_6$alkyl, which can be hydrolyzed to a compound of formula (XVII) wherein $G^1$ is oxygen. Alternatively, the reaction may yield a compound of formula (XVII) wherein $G^1$ is oxygen, directly.

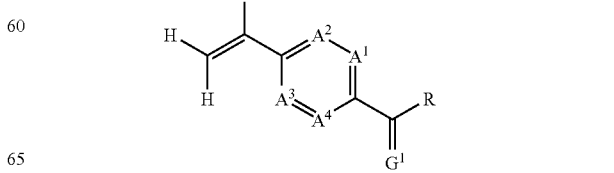

(XVII')

The hydrolysis of the intermediate of formula (XVII') wherein $G^1$ is oxygen, if required, is usually carried out in the presence of an acid, such as hydrochloric acid, in a solvent, such as water or ethyl acetate, or mixtures thereof, at a temperature of from 0° C. to 50° C., preferably at ambient temperature.

Scheme 6

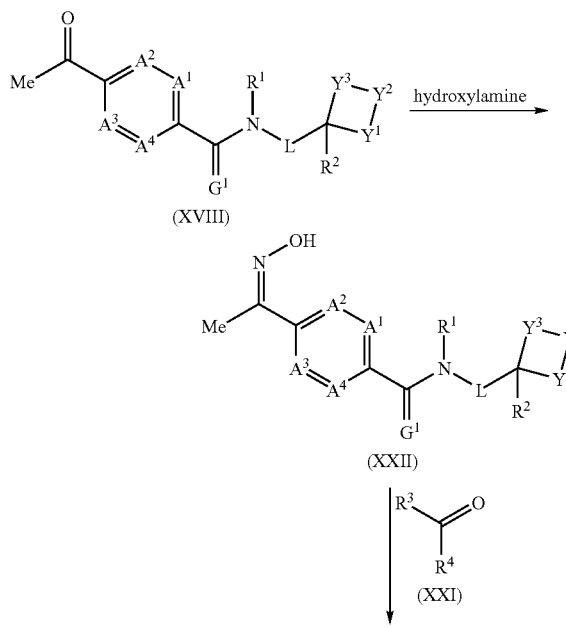

-continued

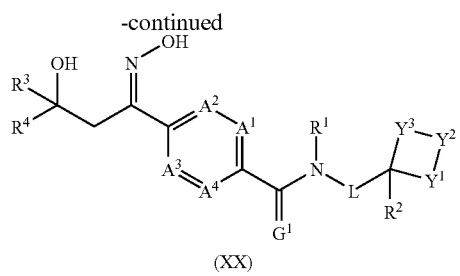

(XX)

27) Alternatively, compounds of formula (XX) wherein $G^1$ is oxygen, can be prepared by reacting a methyl oxime of formula (XXII) wherein $G^1$ is oxygen, with a ketone of formula (XXI) in an aldol-type reaction as shown in Scheme 6. Such reactions are usually carried out by treating the methyl oxime of formula (XXII) wherein $G^1$ is oxygen, with a base, such as n-butyl lithium, lithium diisopropylamide or lithium hexamethyldisilazide, in a solvent, such as tetrahydrofuran, at a temperature of from −78° C. to ambient temperature, preferably from −20° C. to 0° C., followed by addition of the ketone of formula (XXI) at a temperature of from −78° C. to 0° C., preferably at 0° C. Representative conditions for such a transformation can be found in Synthetic Communications 2003, 23, 4163-4171.

28) Compounds of formula (XXII) wherein $G^1$ is oxygen, can be made by reaction of a methyl ketone of formula (XVIII) wherein $G^1$ is oxygen, with a hydroxylamine as described under 23).

Scheme 7

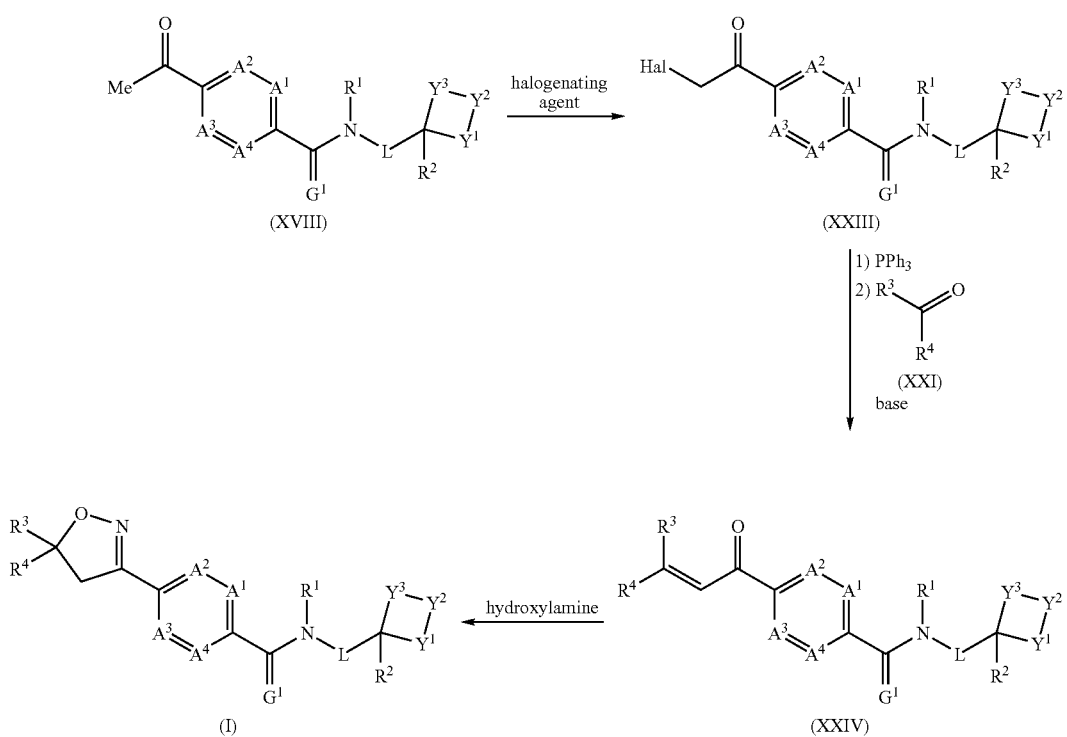

29) Alternatively, compounds of formula (I) wherein $G^1$ is oxygen, can be obtained by reacting an unsaturated ketone of formula (XXIV) wherein $G^1$ is oxygen, with a hydroxylamine, such as hydroxylamine hydrochloride, as shown on Scheme 7. Such reactions can be performed optionally in the presence of a base, such as sodium hydroxide or potassium hydroxide, in a solvent, such as methanol, ethanol or water, or mixtures thereof, at a temperature of from 0° C. to 100° C., preferably from ambient temperature to 80° C. Such conditions are described, for example, in J. Indian Chemical Society 1988, 65(9), 640-2. Such reactions may optionally lead to novel intermediates of formula (XXIV')

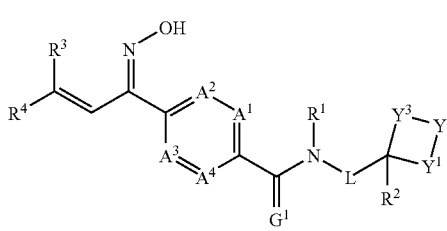

(XXIV')

Such intermediates can be converted into compounds of formula (I) in the presence of an acid, such as hydrochloric acid or acetic acid, or mixtures thereof, or a base, such as sodium methoxide, optionally in a solvent, such as methanol or diethyl ether, at a temperature of from 0° C. to 100° C. Representative procedures for this reaction are described in Eur. J. Org. Chem. 2002, p 1919.

30) Compounds of formula (XXIV) wherein $G^1$ is oxygen, can be obtained by various methods. For example, they can be prepared by reacting in a first step a compound of formula (XXIII) wherein $G^1$ is oxygen and Hal is a halogen, such as bromo or chloro, with a phosphine, such as triphenylphosphine. Such reactions are usually performed in a solvent, such as toluene, at a temperature of from ambient temperature to 150° C., preferably from 80° C. to 120° C. In a second step, the intermediate is treated with a ketone of formula (XXI) and a base, such as n-butyl lithium or triethylamine, in a solvent, such as tetrahydrofuran, at a temperature of from −78° C. to +100° C., preferably from ambient temperature to +80° C. Such conditions are described, for example, in Journal of Organic Chemistry 2006, 71(9), 3545-3550.

31) Compounds of formula (XXIII) wherein $G^1$ is oxygen and Hal is a halogen, such as bromo or chloro, can be prepared by reacting a methyl ketone of formula (XVIII) wherein $G^1$ is oxygen, with a halogenating agent, such as bromine or chlorine, in a solvent, such as acetic acid, at a temperature of from 0° C. to 50° C., preferably from ambient temperature to 40° C.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides fells* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus,* and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifiying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;
b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;
c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;
d) Benzoyl ureas, such as diflubenzuron, triflumuron, hexaflumuron, flufenoxuron or chlorfluazuron;
e) Organic tin compounds, such as cyhexatin, fenbutatin oxide or azocyclotin;
f) Pyrazoles, such as tebufenpyrad and fenpyroximate;
g) Macrolides, such as avermectins or milbemycins, for example abamectin, emamectin benzoate, ivermectin, milbemycin, spinosad, azadirachtin or spinetoram;
h) Hormones or pheromones;
i) Organochlorine compounds, such as endosulfan (in particular alpha-endosulfan), benzene hexachloride, DDT, chlordane or dieldrin;
j) Amidines, such as chlordimeform or amitraz;
k) Fumigant agents, such as chloropicrin, dichloropropane, methyl bromide or metam;
l) Neonicotinoid compounds, such as imidacloprid, thiacloprid, acetamiprid, nitenpyram, dinotefuran, thiamethoxam, clothianidin, nithiazine or flonicamid;
m) Diacylhydrazines, such as tebufenozide, chromafenozide or methoxyfenozide;
n) Diphenyl ethers, such as diofenolan or pyriproxifen;
o) Indoxacarb;
p) Chlorfenapyr;
q) Pymetrozine;
r) Spirotetramat, spirodiclofen or spiromesifen;
s) Diamides, such as flubendiamide, chlorantraniliprole (Rynaxypyr®) or cyantraniliprole;
t) Sulfoxaflor; or
u) Metaflumizone.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy) propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, $CGA^{41396}$, $CGA^{41397}$, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)—N-benzyl-N-([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-A1, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, triclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The following Examples illustrate, but do not limit, the invention.

PREPARATION EXAMPLES

Example I1

Preparation of 4-bromo-3-methyl-benzaldehyde

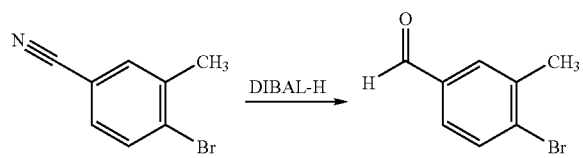

A solution of 4-bromo-3-methyl-benzonitrile (commercially available) (500 mg) in dichloromethane was added at 0° C. to a solution of diisobutylaluminium hydride ("DIBAL-H") (2.6.ml) in hexanes (1M). The mixture was stirred at 0° C. for 2 hours. The reaction mixture was poured on a mixture of ice (10 g) and aqueous hydrobromic acid (6M) (10 ml). The mixture was allowed to warm to ambient temperature and then extracted twice with dichloromethane. The combined organic phases were washed with water, dried over sodium sulfate, and concentrated to give 4-bromo-3-methyl-benzaldehyde (0.419 g) as a colorless oil. $^1$H-NMR (400 MHz, CDCl$_3$): 9.95 (s, 1H), 7.72 (m, 2H), 7.55 (d, 1H), 2.50 (s, 3H) ppm.

Example I2

Preparation of 4-bromo-3-methyl-benzaldehyde oxime

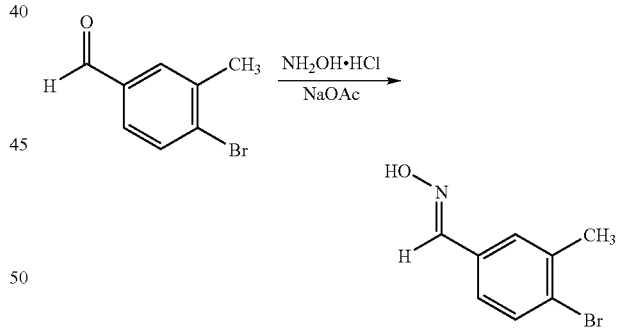

To a solution of 4-bromo-3-methyl-benzaldehyde (4.3 g) (Example I1) in ethanol (50 ml), were added at ambient temperature hydroxylamine hydrochloride (1.75 g), sodium acetate (2.07 g) and water (15 ml). The reaction mixture was stirred at ambient temperature for 3 hours. The reaction mixture was concentrated and the residue diluted with ethyl acetate and aqueous sodium hydroxide (2M). The phases were separated and the organic phase was washed with brine, dried over sodium sulfate, and concentrated. The residue was purified by chromatography on silica gel (eluent: cyclohexane/ethyl acetate 4:1) to give 4-bromo-3-methyl-benzaldehyde oxime (3.65 g) as a white solid. $^1$H-NMR (400 MHz, CDCl$_3$): 8.05 (s, 1H), 7.50 (m, 2H), 7.25 (d, 1H), 2.40 (s, 3H) ppm.

Example I3

Preparation of 3-(4-bromo-3-methyl-phenyl)-5-(3,5-dichloro-phenyl)-5-trifluoromethyl-4,5-dihydro-isoxazole

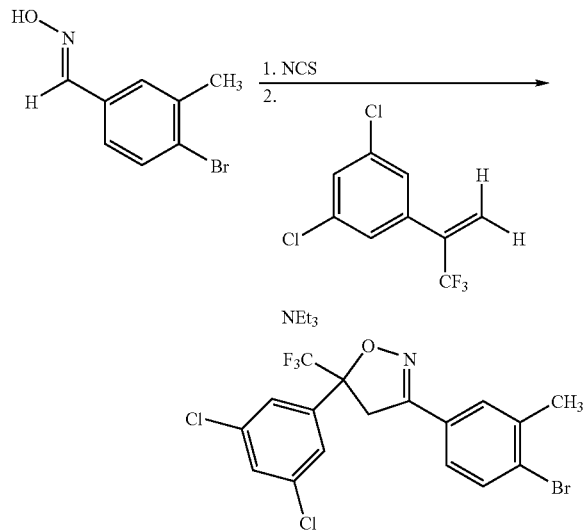

4-Bromo-3-methyl-benzaldehyde oxime (1.3 g) (Example I2) and N-chlorosuccinimide ("NCS") (1.8 g) were dissolved in N,N-dimethylformamide (15 ml). The reaction mixture was stirred at ambient temperature for 90 minutes. A solution of 1,3-dichloro-5-(1-trifluoromethyl-vinyl)-benzene (1.3 g) (prepared according to WO 2005/085216) and triethylamine (1.9 ml) in N,N-dimethylformamide (15 ml) was added and the reaction mixture was stirred at ambient temperature for 18 hours. The reaction mixture was diluted with water and ethyl acetate and the phases were separated. The organic phase was washed twice with water and the aqueous phases were extracted twice with ethyl acetate. The combined organic phases were dried over sodium sulfate and concentrated. The residue was purified by chromatography on silica gel (eluent: cyclohexane/dichloromethane 4:1) to give 3-(4-bromo-3-methyl-phenyl)-5-(3,5-dichloro-phenyl)-5-trifluoromethyl-4,5-dihydro-isoxazole (1.57 g). $^1$H-NMR (400 MHz, CDCl$_3$): 7.40 (m, 6H), 4.05 (d, 1H), 3.65 (d, 1H), 2.40 (s, 3H) ppm.

Example I4

Preparation of 4-[5-(3,5-dichloro-phenyl)-5-trifluoromethyl-4,5-dihydro-isoxazol-3-yl]-2-methyl-benzoic acid ethyl ester

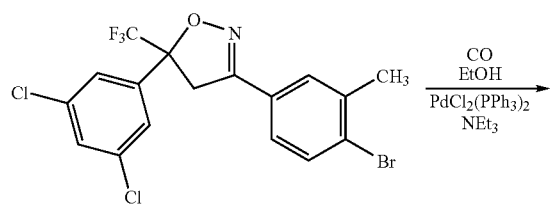

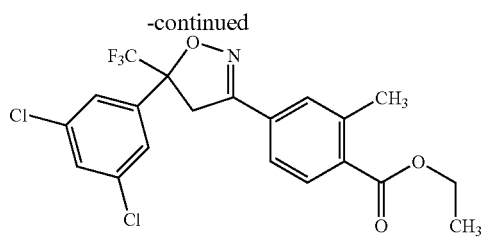

Triethylamine (1.2 ml) was added at ambient temperature to a solution of 3-(4-bromo-3-methyl-phenyl)-5-(3,5-dichloro-phenyl)-5-trifluoromethyl-4,5-dihydro-isoxazole (1.2 g) (Example I3) in ethanol (45 ml). Bis(triphenylphosphine)palladium(II) dichloride ("PdCl$_2$(PPh$_3$)$_2$") (0.185 g) was added and the reaction mixture was stirred in a pressure reactor in an atmosphere of carbon monoxide (120 bar) at 115° C. for 8 hours. The reaction mixture was cooled to ambient temperature, filtered over Celite® and concentrated. The residue was purified by preparative HPLC to give 4-[5-(3,5-dichloro-phenyl)-5-trifluoromethyl-4,5-dihydro-isoxazol-3-yl]-2-methyl-benzoic acid ethyl ester (0.85 g) as a yellow oil. $^1$H-NMR (CDCl$_3$, 400 MHz): 7.95 (d, 1H), 7.55 (m, 4H), 7.45 (s, 1H), 4.40 (q, 2H), 4.10 (d, 1H), 3.7 (d, 1H), 2.60 (s, 3H), 1.40 (t, 3H) ppm.

Example I5

Preparation of 4-[5-(3,5-dichloro-phenyl)-5-trifluoromethyl-4,5-dihydro-isoxazol-3-yl]-2-methyl-benzoic acid

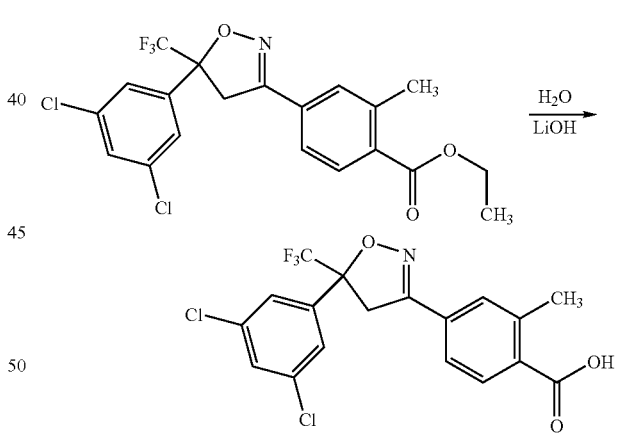

Lithium hydroxide (51 mg) was added at ambient temperature to a solution of 4-[5-(3,5-dichloro-phenyl)-5-trifluoromethyl-4,5-dihydro-isoxazol-3-yl]-2-methyl-benzoic acid ethyl ester (0.27 g) (Example I4) in tetrahydrofuran (3 ml) and water (0.75 ml). The reaction mixture was stirred at 50° C. for 18 hours. The reaction mixture was cooled to ambient temperature and diluted with water, acidified by addition of aqueous hydrochloric acid (2M) and extracted three times with ethyl acetate. The combined organic phases were washed with brine, dried over sodium sulfate and concentrated to give 4-[5-(3,5-dichloro-phenyl)-5-trifluoromethyl-4,5-dihydro-isoxazol-3-yl]-2-methyl-benzoic acid (0.25 g), which was used without further purification. $^1$H-NMR (DMSO-d6, 400 MHz): 13.1 (s, 1H), 7.90 (d, 1H), 7.80 (s, 1H), 7.65 (m, 4H), 4.40 (m, 2H), 2.55 (s, 3H).

Example I6

Preparation of 4-[5-(3,5-dichloro-phenyl)-5-trifluoromethyl-4,5-dihydro-isoxazol-3-yl]-2-methyl-benzoic acid methyl ester

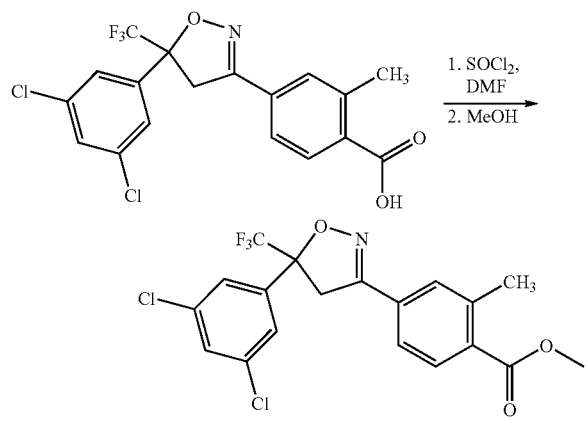

To a suspension 4-[5-(3,5-dichloro-phenyl)-5-trifluoromethyl-4,5-dihydro-isoxazol-3-yl]-2-methyl-benzoic acid (Example I5) (10 g) in toluene (150 ml) and dimethylformamide (0.1 ml) at ambient temperature was added dropwise thionyl chloride (3.5 ml). The reaction mixture was stirred at 50° C. for 2 hours. The solution was then cooled to 0° C. and methanol (2 ml) added slowly. The reaction mixture was stirred at ambient temperature for 1 hour. The reaction mixture was concentrated and aqueous sodium hydrogen carbonate (saturated) (50 ml) added to the residue. The mixture was extracted with ethyl acetate (3×100 ml). The combined organic extracts were dried over sodium sulfate and concentrated to afford 4-[5-(3,5-dichloro-phenyl)-5-trifluoromethyl-4,5-dihydro-isoxazol-3-yl]-2-methyl-benzoic acid methyl ester as a yellow solid (11.5 g). $^1$H-NMR (CDCl$_3$, 400 MHz): 7.95 (d, 1H), 7.55 (m, 4H), 7.45 (s, 1H), 4.10 (d, 1H), 3.90 (s, 3H), 3.70 (d, 1H), 2.60 (s, 3H) ppm.

Example I7

Preparation of 4-bromomethyl-2-trifluoromethyl-benzoic acid

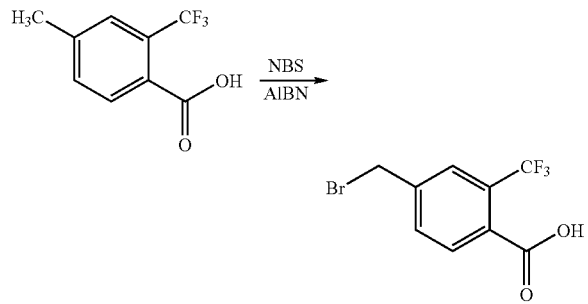

A suspension of 4-methyl-2-trifluoromethyl-benzoic acid (commercially available) (20.242 g), N-bromosuccinimide ("NBS") (19.52 g) and 2,2'-azobis-(2-methylpropanenitrile) ("AIBN") (0.859 g) in α,α,α-trifluorotoluene (160 ml) was heated to 90° C. for 1.5 hours. The reaction mixture was allowed to cool to ambient temperature and then diluted with ethyl acetate (200 ml) and aqueous hydrochloric acid (1M) (100 ml). The phases were separated and the organic phase was washed with aqueous hydrochloric acid (1M) (100 ml) and brine (150 ml), dried over sodium sulfate and concentrated. The residue was triturated with dichloromethane (40 ml). The solids were isolated by filtration and dried to give 4-bromomethyl-2-trifluoromethyl-benzoic acid (5.01 g) as a white powder. The filtrate was concentrated, re-dissolved in heptane/dichloromethane (1:1) (40 ml) and the dichloromethane slowly evaporated to initiate crystallization. The solids were isolated by filtration, rinsed with pentane and dried to give a second fraction of 4-bromomethyl-2-trifluoromethyl-benzoic acid (7.00 g) as a white powder. $^1$H-NMR (CDCl$_3$, 400 MHz): 11.5 (br s, 1H), 8.03-7.20 (m, 3H), 4.52 (s, 2H).

Similarly, 2-bromo-4-bromomethyl-benzoic acid was obtained from 2-bromo-4-methyl-benzoic acid (commercially available). $^1$H-NMR (DMSO-d6, 400 MHz): 13.54 (br s, 1H), 7.86-7.56 (m, 3H), 4.76 (s, 2H).

Example I8

Preparation of 4-hydroxymethyl-2-trifluoromethyl-benzoic acid

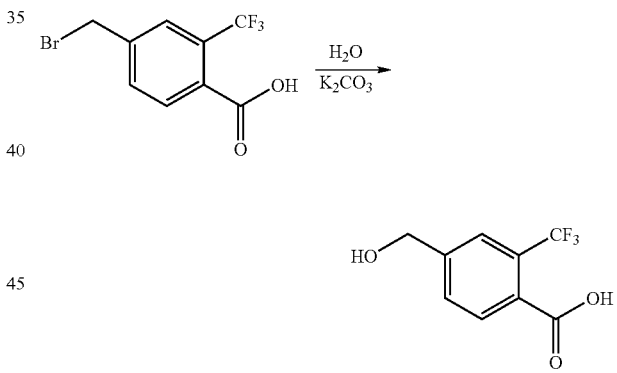

To a suspension of 4-bromomethyl-2-trifluoromethyl-benzoic acid (Example I7) (13.03 g) in water (200 ml) was added potassium carbonate (31.1 g). The reaction mixture was stirred at 95° C. for 1 hour. The reaction mixture was then allowed to cool to ambient temperature and was quenched by addition of aqueous hydrochloric acid (5M) (250 ml). The mixture was extracted with ethyl acetate (3×150 ml). The extracts were dried over sodium sulfate and concentrated. The residue was crystallized from ethyl acetate and heptane to give 4-hydroxymethyl-2-trifluoromethyl-benzoic acid (9.07 g) as a white crystalline powder. $^1$H-NMR (DMSO-d6, 400 MHz): 13.5 (br s, 1H), 7.81-7.66 (m, 3H), 5.53 (s, 1H), 4.62 (s, 2H).

Similarly, 2-bromo-4-hydroxymethyl-benzoic acid was obtained from 2-bromo-4-bromomethyl-benzoic acid (Example I7). $^1$H-NMR (DMSO-d6, 400 MHz): 13.36 (br s, 1H), 7.77-7.41 (m, 3H), 5.48 (s, 1H), 4.57 (s, 2H).

Example I9

Preparation of 4-hydroxymethyl-2-trifluoromethyl-benzoic acid methyl ester

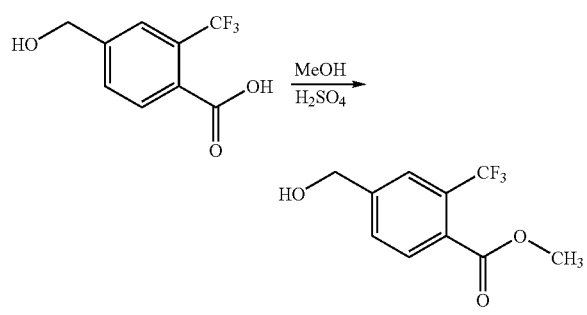

To a solution of 4-hydroxymethyl-2-trifluoromethyl-benzoic acid (Example I8) (9.07 g) in methanol (250 ml) was added toluene (250 ml) and concentrated sulfuric acid (4.5 ml). The reaction mixture was stirred at 80° C. for 16 hours. The methanol was removed and the residue diluted with aqueous sodium hydrogen carbonate (saturated) (150 ml) and ethyl acetate (150 ml). The phases were separated and the aqueous layer was extracted with more ethyl acetate (2×150 ml). The combined organic extracts were washed with brine, dried over sodium sulfate and concentrated to give 4-hydroxymethyl-2-trifluoromethyl-benzoic acid methyl ester (5.97 g) as a colorless oil. $^1$H-NMR (CDCl$_3$, 400 MHz): 8.76-7.27 (m, 3H), 4.78 (s, 2H), 3.93 (s, 3H), 2.5 (br s, 1H).

Similarly, 2-bromo-4-hydroxymethyl-benzoic acid methyl ester was obtained from 2-bromo-4-hydroxymethyl-benzoic acid (Example I8). $^1$H-NMR (CDCl$_3$, 400 MHz): 7.81-7.33 (m, 3H), 4.73 (s, 2H), 3.93 (s, 2.0 (br s, 1H).

Example I10

Preparation of 4-formyl-2-trifluoromethyl-benzoic acid methyl ester

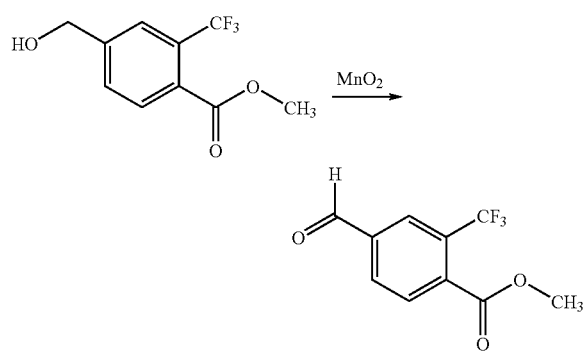

To a solution of 4-hydroxymethyl-2-trifluoromethyl-benzoic acid methyl ester (Example I9) (7.15 g) in dichloromethane (150 ml) was added manganese dioxide (25.1 g). The reaction mixture stirred at ambient temperature for 2.5 hours. The reaction mixture was filtered over a plug of silica gel and the filtrate concentrated to give 4-formyl-2-trifluoromethyl-benzoic acid methyl ester (5.98 g), which was used without further purification. $^1$H-NMR (CDCl$_3$, 400 MHz): 10.11 (s, 1H), 8.25-7.59 (m, 3H), 3.98 (s, 3H).

Similarly, 2-bromo-4-formyl-benzoic acid methyl ester was obtained from 2-bromo-4-hydroxymethyl-benzoic acid methyl ester (Example I9). $^1$H-NMR (CDCl$_3$, 400 MHz): 10.04 (s, 1H), 8.14-7.85 (m, 3H), 3.97 (s, 3H).

Example I11

Preparation of 4-(hydroxyimino-methyl)-2-trifluoromethyl-benzoic acid methyl ester

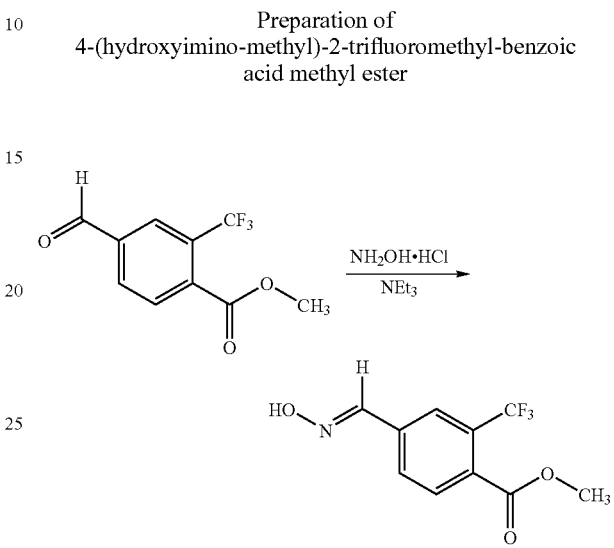

To a suspension of 4-formyl-2-trifluoromethyl-benzoic acid methyl ester (Example I10) (5.98 g) and hydroxylamine hydrochloride (1.79 g) in methanol (80 ml) was added triethylamine (5.4 ml). The reaction mixture was stirred at ambient temperature for 1 hour. More hydroxylamine hydrochloride (5.4 g) was added and the reaction mixture was stirred at ambient temperature for 16 hours. The solvent was removed and the residue diluted with ethyl acetate (200 ml) and water (150 ml). The phases were separated and the organic layer was washed with brine (100 ml), dried over sodium sulfate and concentrated. The residue was dissolved in a mixture of dichloromethane and heptane and crystallized by slowly evaporating the dichloromethane to give 4-(hydroxyimino-methyl)-2-trifluoromethyl-benzoic acid methyl ester (3.90 g) as a white crystalline powder. $^1$H-NMR (CDCl$_3$, 400 MHz): 8.18 (s, 1H), 7.97-7.64 (m, 4H), 3.95 (s, 3H).

Similarly, 2-bromo-4-(hydroxyimino-methyl)-benzoic acid methyl ester was obtained from 2-bromo-4-formyl-benzoic acid methyl ester (Example I10). $^1$H-NMR (CDCl$_3$, 400 MHz): 8.08 (s, 1H), 7.89-7.54 (m, 4H), 3.95 (s, 3H).

Example I12

Preparation of 4-(chloro(hydroxyimino)methyl)-2-trifluoromethyl-benzoic acid methyl ester

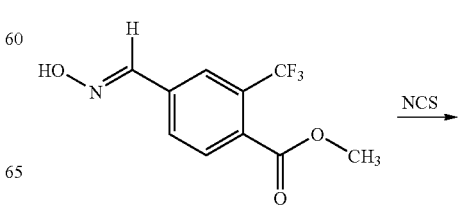

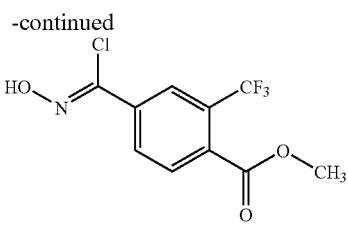

To a solution of 4-(hydroxyimino-methyl)-2-trifluoromethyl-benzoic acid methyl ester (Example I11) (3.90 g) in N,N-dimethylformamide (20 ml) was added N-chlorosuccinimide ("NCS") (2.318 g). The reaction mixture was stirred at ambient temperature for 45 minutes. The reaction mixture was poured into water (400 ml). The solids were isolated by filtration and dried to give 4-(chloro(hydroxyimino)methyl)-2-trifluoromethyl-benzoic acid methyl ester (4.21 g) as an off-white powder. $^1$H-NMR (CDCl$_3$, 400 MHz): 9.00 (s, 1H), 8.24-8.04 (m, 3H), 3.96 (s, 3H).

Similarly, 2-bromo-4-(chloro(hydroxyimino))-benzoic acid methyl ester was obtained from 2-bromo-4-(hydroxyimino-methyl)-benzoic acid methyl ester (Example I11). $^1$H-NMR (CDCl$_3$, 400 MHz): 8.92 (s, 1H), 8.16-7.83 (m, 3H), 3.96 (s, 3H).

Example I13

Preparation of 4-[5-(3,5-dichloro-phenyl)-5-trifluoromethyl-4,5-dihydro-isoxazol-3-yl]-2-trifluoromethyl-benzoic acid methyl ester

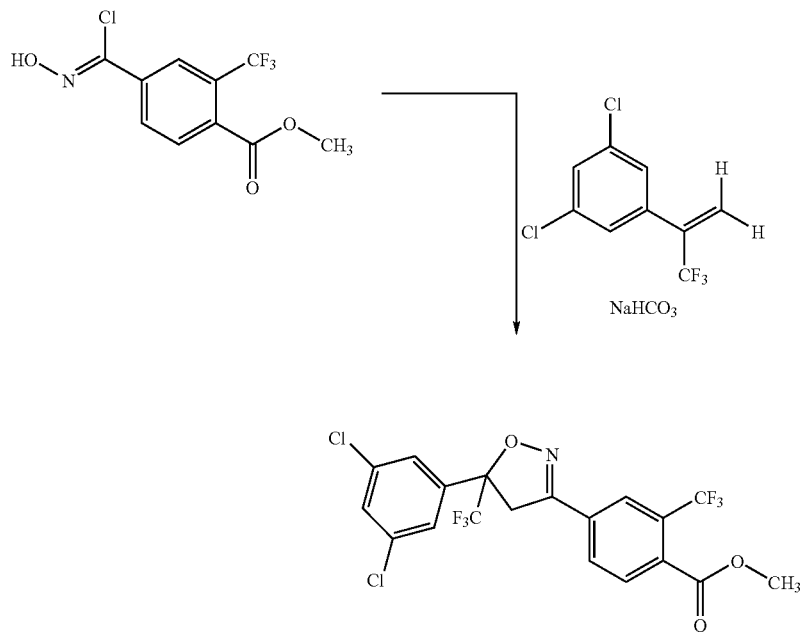

To a solution of 4-(chloro(hydroxyimino)methyl)-2-trifluoromethyl-benzoic acid methyl ester (Example I12) (4.21 g) in isopropanol (100 ml) was added sequentially sodium hydrogen carbonate (2.90 g) and 1,3-dichloro-5-(1-trifluoromethyl-vinyl)-benzene (4.22 g) (prepared according to WO 2005/085216). The reaction mixture was stirred at 60° C. for 16 hours. The isopropanol was removed by distillation. The residue was purified over silica gel (eluent: ethyl acetate/heptane gradient from 0:1 to 2:3) to give 4-[5-(3,5-dichlorophenyl)-5-trifluoromethyl-4,5-dihydro-isoxazol-3-yl]-2-trifluoromethyl-benzoic acid methyl ester (4.30 g). $^1$H-NMR (CDCl$_3$, 400 MHz): 8.00-7.44 (m, 6H), 4.12 (d, 1H), 3.96 (s, 3H), 3.74 (d, 1H).

Similarly, 2-bromo-4-[5-(3,5-dichloro-phenyl)-5-trifluoromethyl-4,5-dihydro-isoxazol-3-yl]-benzoic acid methyl ester was obtained from 2-bromo-4-(chloro(hydroxy-imino)methyl)-benzoic acid methyl ester (Example I12). $^1$H-NMR (CDCl$_3$, 400 MHz): 7.92-7.43 (m, 6H), 4.08 (d, 1H), 3.95 (s, 3H), 3.70 (d, 1H).

Example I14

Preparation of 2-cyano-4-[5-(3,5-dichloro-phenyl)-5-trifluoromethyl-4,5-dihydro-isoxazol-3-yl]-benzoic acid methyl ester

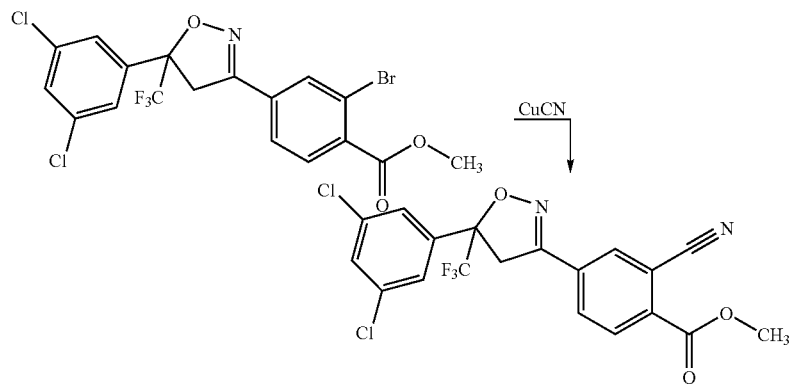

To a solution of 2-bromo-4-[5-(3,5-dichloro-phenyl)-5-trifluoromethyl-4,5-dihydro-isoxazol-3-yl]-benzoic acid methyl ester (Example I13) (2.52 g) in dry N,N-dimethylformamide (75 ml) was added copper(I) cyanide (1.145 g). The reaction mixture was stirred at 160° C. for 40 minutes. The reaction mixture was allowed to cool to ambient temperature and was poured into a mixture of aqueous sodium carbonate (saturated) and water (1:2) (150 ml). The mixture was extracted with ethyl acetate (3×70 ml). The combined organic extracts were washed with water (2×70 ml) and brine (70 ml), dried over sodium sulfate and concentrated. The residue was re-crystallized from a mixture of diethyl ether and heptane (1:1) to give methyl 2-cyano-4-[5-(3,5-dichloro-phenyl)-5-trifluoromethyl-4,5-dihydro-isoxazol-3-yl]-benzoic acid methyl ester (1.474 g). $^1$H-NMR (CDCl$_3$, 400 MHz): 8.23-7.45 (m, 6H), 4.11 (d, 1H), 4.03 (s, 3H), 3.74 (d, 1H).

Example I15

Preparation of 4-[5-(3,5-dichloro-phenyl)-5-trifluoromethyl-4,5-dihydro-isoxazol-3-yl]-2-trifluoromethyl-benzoic acid To a solution of 4-[5-(3,5-dichloro-phenyl)-5-trifluoromethyl-4,5-dihydro-isoxazol-3-yl]-2-trifluoromethyl-benzoic acid methyl ester (Example I13) (4.3 g) in tetrahydrofuran (3 ml) and methanol (3 ml) was added a solution of potassium hydroxide (1.0 g) in water (4.0 ml). The reaction mixture was stirred at ambient temperature for 2 hours. The reaction mixture was acidified by addition of hydrochloric acid (2M) (200 ml) and the mixture extracted with ethyl acetate (3×100 ml). The combined organic extracts were washed with brine, dried over sodium sulfate and concentrated. The residue was re-crystallized from dichloromethane and heptane to give 4-[5-(3,5-dichloro-phenyl)-5-trifluoromethyl-4,5-dihydro-isoxazol-3-yl]-2-trifluoromethyl-benzoic acid (3.58 g) as a white powder. $^1$H-NMR (CDCl$_3$, 400 MHz): 8.08-7.45 (m, 6H), 4.14 (d, 1H), 3.76 (d, 1H).

Similarly, 2-bromo-4-[5-(3,5-dichloro-phenyl)-5-trifluoromethyl-4,5-dihydro-isoxazol-3-yl]-benzoic acid was obtained from 2-bromo-4-[5-(3,5-dichloro-phenyl)-5-trifluoromethyl-4,5-dihydro-isoxazol-3-yl]-benzoic acid methyl ester (Example I13). $^1$H-NMR (DMSO-d6, 400 MHz): 13.74 (br s, 1H), 8.00-7.62 (m, 6H), 4.41 (m, 2H).

Similarly, 2-cyano-4-[5-(3,5-dichloro-phenyl)-5-trifluoromethyl-4,5-dihydro-isoxazol-3-yl]-benzoic acid was obtained from 2-cyano-4-[5-(3,5-dichloro-phenyl)-5-trifluoromethyl-4,5-dihydro-isoxazol-3-yl]-benzoic acid methyl ester (Example I14). $^1$H-NMR (DMSO-d6, 400 MHz): 14.15 (br s, 1H), 8.24-7.62 (m, 6H), 4.52 (d, 1H), 4.42 (d, 1H).

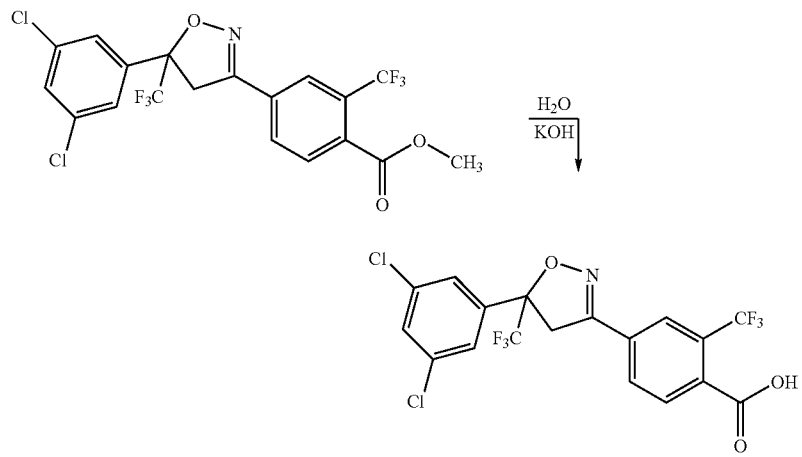

Example I16

Preparation of 4-bromo-2-methyl-benzoic acid tert-butyl ester

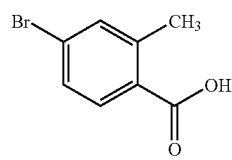

1. (COCl)₂, DMF
2. KOtBu

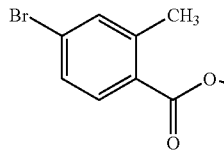

4-Bromo-2-methyl-benzoic acid (commercially available) (50 g) was suspended in dichloromethane (500 ml). A catalytic amount of N,N-dimethylformamide ("DMF") and oxalyl chloride (23 ml) were added to the suspension. The reaction mixture was stirred at ambient temperature for 3 hours. The reaction mixture was concentrated and the residue dissolved in dry tetrahydrofuran (800 ml). The solution was cooled to 2° C. and added to a solution of potassium tert-butoxide (39.2 g) in dry tetrahydrofuran (300 ml) dropwise at 5-10° C. The reaction mixture was stirred at ambient temperature for 30 minutes and then poured onto a mixture of ice and water. The mixture was extracted with ethyl acetate. The organic extract was washed with water, dried over sodium sulfate and concentrated to give 4-bromo-2-methyl-benzoic acid tert-butyl ester (65.3 g) as a yellow oil, which was used without further purification. ¹H-NMR (CDCl₃, 400 MHz): 7.70 (d, 1H), 7.40 (s, 1H), 7.35 (d, 1H), 2.58 (s, 3H), 1.60 (s, 9H).

Example I17

Preparation of 4-formyl-2-methyl-benzoic acid tert-butyl ester

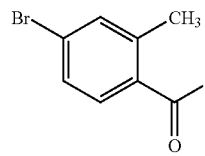

DMF / BuLi

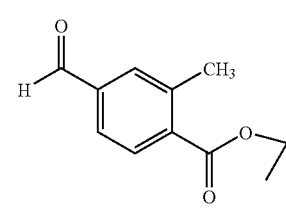

A solution of 4-bromo-2-methyl-benzoic acid tert-butyl ester (Example I16) (75 g) in dry tetrahydrofuran (750 ml) was cooled to −100° C. A solution of n-butyl lithium (1.6 M in hexane) (163 ml) was added dropwise at −100° C. The reaction mixture was stirred at −95° C. for 20 minutes. N,N-Dimethylformamide (43 ml) was added dropwise. The reaction mixture was stirred at −95° C. for 45 minutes. The reaction was quenched by addition of aqueous ammonium chloride (saturated) (8 ml) at −90° C. The mixture was stirred for 10 minutes at −90° C., warmed to 0° and poured on a mixture of ice and water. The mixture was allowed to warm to ambient temperature and then extracted twice with ethyl acetate. The combined organic phases were washed with water, dried over sodium sulfate, and concentrated to give 4-formyl-2-methyl-benzoic acid tert-butyl ester (60.3 g) as yellow oil. ¹H-NMR (CDCl₃, 400 MHz): 10.03 (s, 1H), 7.93 (d, 1H), 7.75 (m, 2H), 2.65 (s, 3H), 1.65 (s, 9H).

Example I18

Preparation of 4-(hydroxyimino-methyl)-2-methyl-benzoic acid tert-butyl ester

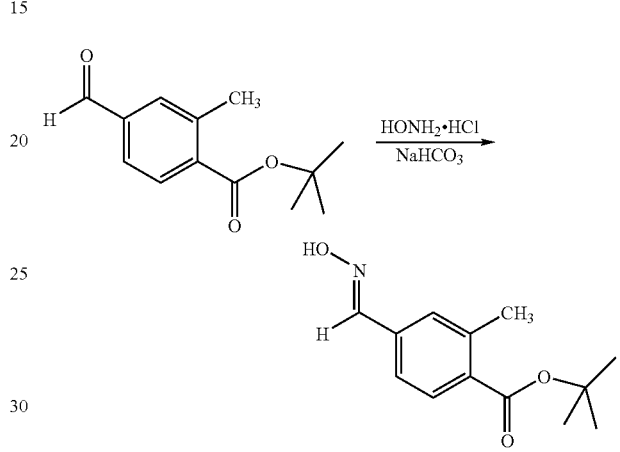

To a suspension of 4-formyl-2-methyl-benzoic acid tert-butyl ester (Example I17) (60.3 g) and hydroxylamine hydrochloride (38.05 g) in ethanol (580 ml) was added a solution of sodium hydrogen carbonate (46 g) in water (60 ml). The reaction mixture was stirred at 50° C. for 3.5 hours. The solvent was removed and the residue diluted with ethyl acetate and water. The phases were separated and the organic layer was washed with water, dried over sodium sulfate and concentrated. The residue was crystallized from ethyl acetate and heptane to give 4-(hydroxyimino-methyl)-2-methyl-benzoic acid tert-butyl ester (35.72 g) as a white crystalline powder. ¹H-NMR (CDCl₃, 400 MHz): 7.86 (s, 1H), 7.70 (s, 1H), 7.45 (m, 2H), 2.60 (s, 3H), 1.60 (s, 9H).

Example I19

Preparation of 4-[5-(3,5-dichloro-phenyl)-5-trifluoromethyl-4,5-dihydro-isoxazol-3-yl]-2-methyl-benzoic acid tert-butyl ester

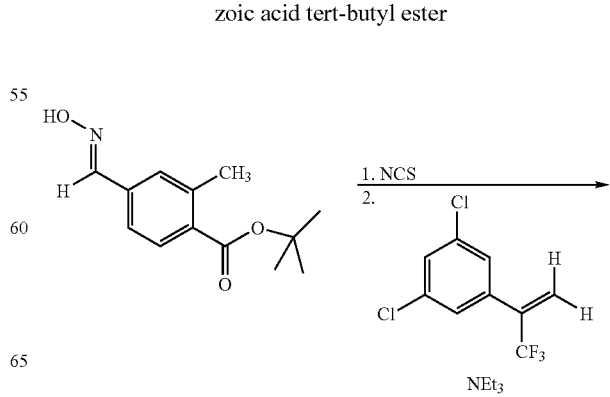

1. NCS
2. NEt₃

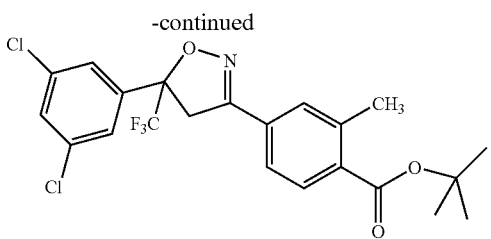

To a solution of 4-(hydroxyimino-methyl)-2-methyl-benzoic acid tert-butyl ester (Example I18) (32.5 g) in N,N-dimethylformamide (280 ml) was added N-chlorosuccinimide ("NCS") (18.44 g). The reaction mixture was stirred at ambient temperature for 3.5 hour. A solution of 1,3-dichloro-5-(1-trifluoromethyl-vinyl)-benzene (33.3 g) (prepared according to WO 2005/085216) and triethylamine (19.25 ml) in N,N-dimethylformamide (220 ml) was added dropwise to the reaction mixture. The reaction mixture was stirred at ambient temperature for 16 hours. Water and ethyl acetate were added and the phases were separated. The organic layer was washed with water, dried over sodium sulfate and concentrated. The residue was crystallized from ethyl acetate and heptane to give 4-[5-(3,5-dichloro-phenyl)-5-trifluoromethyl-4,5-dihydro-isoxazol-3-yl]-2-methyl-benzoic acid tert-butyl ester (40.12 g). $^1$H-NMR (CDCl$_3$, 400 MHz): 7.88 (d, 1H), 7.55-7.45 (m, 5H), 4.10 (d, 1H), 3.75 (d, 1H), 2.60 (s, 3H), 1.65 (s, 9H).

Similarly, 2-methyl-4-[5-trifluoromethyl-5-(3-trifluoromethyl-phenyl)-4,5-dihydro-isoxazol-3-yl]-benzoic acid tert-butyl ester was obtained when 1-trifluoromethyl-3-(1-trifluoromethyl-vinyl)-benzene (prepared according to WO 2005/085216) was used as reagent. $^1$H-NMR (CDCl$_3$, 400 MHz): 7.87-7.26 (m, 7H), 4.14 (d, 1H), 3.75 (d, 1H), 2.59 (s, 3H), 1.60 (s, 9H).

Similarly, 4-[5-(3,5-bis-trifluoromethyl-phenyl)-5-trifluoromethyl-4,5-dihydro-isoxazol-3-yl]-2-methyl-benzoic acid tert-butyl ester was obtained when 1,3-bis-trifluoromethyl-5-(1-trifluoromethyl-vinyl)-benzene (prepared according to WO 2005/085216) was used as reagent. $^1$H-NMR (CDCl$_3$, 400 MHz): 8.09-7.52 (m, 6H), 4.21 (d, 1H), 3.76 (d, 1H), 2.59 (s, 3H), 1.60 (s, 9H).

Example I20

Alternative preparation of 4-[5-(3,5-dichloro-phenyl)-5-trifluoromethyl-4,5-dihydro-isoxazol-3-yl]-2-methyl-benzoic acid

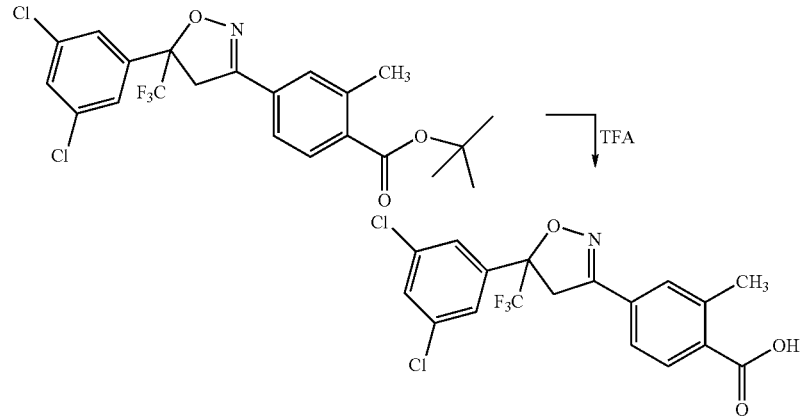

To a solution of 4-[5-(3,5-dichloro-phenyl)-5-trifluoromethyl-4,5-dihydro-isoxazol-3-yl]-2-methyl-benzoic acid tert-butyl ester (Example I19) (74.14 g) in dichloromethane (750 ml) was added trifluoromethyl acetic acid ("TFA") (148 ml). The reaction mixture was stirred at ambient temperature for 16 hours. Ethyl acetate was added and the mixture was washed with water, dried over sodium sulfate and concentrated. The residue was crystallized from ethyl acetate and heptane to give 4-[5-(3,5-dichloro-phenyl)-5-trifluoromethyl-4,5-dihydro-isoxazol-3-yl]-2-methyl-benzoic acid (55.0 g). $^1$H-NMR (CDCl$_3$, 400 MHz): 8.12 (d, 1H), 7.65-7.45 (m, 5H), 4.15 (d, 1H), 3.75 (d, 1H), 2.75 (s, 3H).

Similarly, 4-[5-(3-trifluoromethyl-phenyl)-5-trifluoromethyl-4,5-dihydro-isoxazol-3-yl]-2-methyl-benzoic acid was obtained when 4-[5-(3-trifluoromethyl-phenyl)-5-trifluoromethyl-4,5-dihydro-isoxazol-3-yl]-2-methyl-benzoic acid tert-butyl ester (Example I19) was used as starting material. $^1$H-NMR (DMSO-d6, 400 MHz): 13.16 (s, 1H), 7.96-7.67 (m, 7H), 4.49 (d, 1H), 4.32 (d, 1H), 2.57 (s, 3H).

Similarly, 4-[5-(3,5-bis-trifluoromethyl-phenyl)-5-trifluoromethyl-4,5-dihydro-isoxazol-3-yl]-2-methyl-benzoic acid was obtained when 4-[5-(3,5-bis-trifluoromethyl-phenyl)-5-trifluoromethyl-4,5-dihydro-isoxazol-3-yl]-2-methyl-benzoic acid tert-butyl ester (Example I19) was used as starting material. $^1$H-NMR (DMSO-d6, 400 MHz): 13.18 (s, 1H), 8.35-7.67 (m, 6H), 4.50 (m, 2H), 2.58 (s, 3H).

Example I21

Preparation of 4-[5-(3,5-dichloro-phenyl)-5-trifluoromethyl-4,5-dihydro-isoxazol-3-yl]-2-iodo-6-methyl-benzoic acid

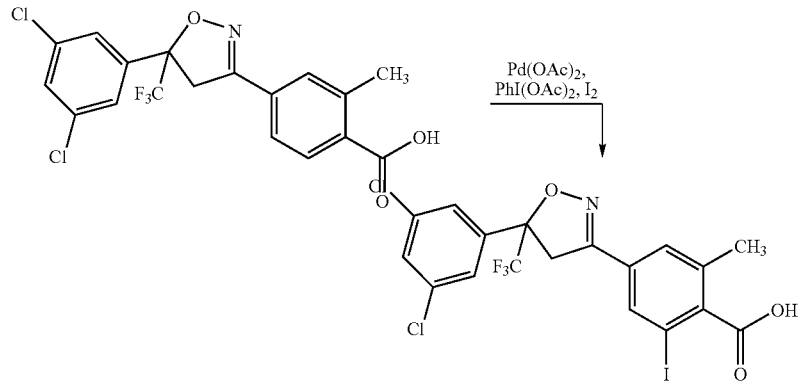

A sealed tube purged with argon was charged with 4-[5-(3,5-dichloro-phenyl)-5-trifluoromethyl-4,5-dihydro-isoxazol-3-yl]-2-methyl-benzoic acid (Example I5) (836 mg), palladium(II) acetate (45 mg), phenyl iododiacetate (1.28 g) and iodine (508 mg). N,N-Dimethylformamide (10 ml) was added and the reaction mixture was stirred at 100° C. for 1 hour. The reaction mixture was cooled to ambient temperature then poured into water. The mixture was extracted three times with ethyl acetate (25 ml). The combined organic extracts were washed with water and brine, then dried over sodium sulfate and concentrated. The residue was purified by chromatography on silica gel (eluent: dichloromethane/methanol) to afford 4-[5-(3,5-dichloro-phenyl)-5-trifluoromethyl-4,5-dihydro-isoxazol-3-yl]-2-iodo-6-methyl-benzoic acid (700 mg) as a yellow solid. $^1$H-NMR (CDCl$_3$, 400 MHz): 7.20-7.80 (m, 6H), 4.05 (d, 1H), 3.70 (d, 1H), 2.25 (s, 3H).

Similarly, 4-[5-(3,5-dichloro-phenyl)-5-trifluoromethyl-4,5-dihydro-isoxazol-3-yl]-2-bromo-6-methyl-benzoic acid was obtained when tetrabutylammonium bromide was used in addition to palladium(II) acetate, phenyl iododiacetate and iodine. $^1$H-NMR (CDCl$_3$, 400 MHz): 7.65 (s, 1H), 7.40 (m, 3H), 7.35 (s, 1H), 4.00 (d, 1H), 3.60 (d, 1H), 2.40 (s, 3H).

Example I22

Preparation of 5-bromo-4-[5-(3,5-dichloro-phenyl)-5-trifluoromethyl-4,5-dihydro-isoxazol-3-yl]-2-methyl-benzoic acid methyl ester A sealed tube purged with argon was charged with 4-[5-(3,5-dichloro-phenyl)-5-trifluoromethyl-4,5-dihydro-isoxazol-3-yl]-2-methyl-benzoic acid methyl ester (Example I6) (432 mg), palladium(II) acetate (23 mg) and N-bromosuccinimide ("NBS") (356 mg). Acetic acid (10 ml) was added and the reaction mixture was stirred at 100° C. for 96 hours. The reaction mixture was cooled to ambient temperature then poured into water. The mixture was extracted three times with ethyl acetate (25 ml). The combined organic extracts were washed with water and brine, dried over sodium sulfate and concentrated. The residue was purified by chromatography on silica gel (eluent: cyclohexane/ethyl acetate) to afford 5-bromo-4-[5-(3,5-dichloro-phenyl)-5-trifluoromethyl-4,5-dihydro-isoxazol-3-yl]-2-methyl-benzoic acid methyl ester (150 mg) as a colorless resin. $^1$H-NMR (CDCl$_3$, 400 MHz): 8.10 (s, 1H), 7.30-7.50 (m, 4H), 4.20 (d, 1H), 3.80 (s, 3H), 3.75 (d, 1H), 2.45 (s, 3H).

Similarly, 5-chloro-4-[5-(3,5-dichloro-phenyl)-5-trifluoromethyl-4,5-dihydro-isoxazol-3-yl]-2-methyl-benzoic acid methyl ester was obtained N-chlorosuccinimide ("NCS") was used instead of N-bromosuccinimide. $^1$H-NMR (CDCl$_3$, 400 MHz): 7.90 (s, 1H), 7.50 (s, 1H), 7.40 (s, 2H), 7.35 (s, 1H), 4.20 (d, 1H), 3.80 (s, 3H), 3.75 (d, 1H), 2.50 (s, 3H).

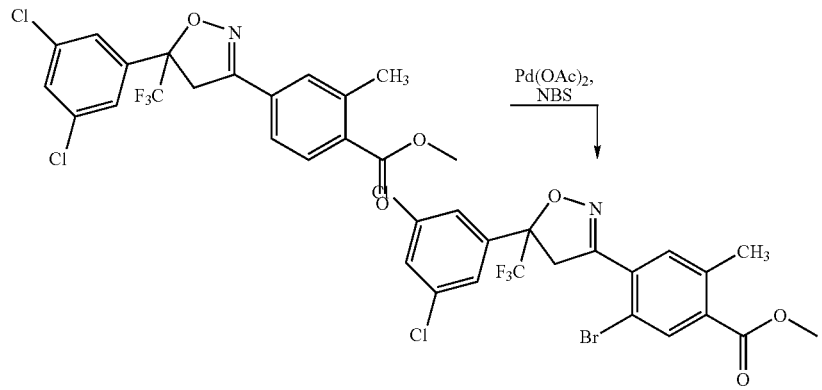

Example I23

Preparation of 5-bromo-4-[5-(3,5-dichloro-phenyl)-5-trifluoromethyl-4,5-dihydro-isoxazol-3-yl]-2-methyl-benzoic acid

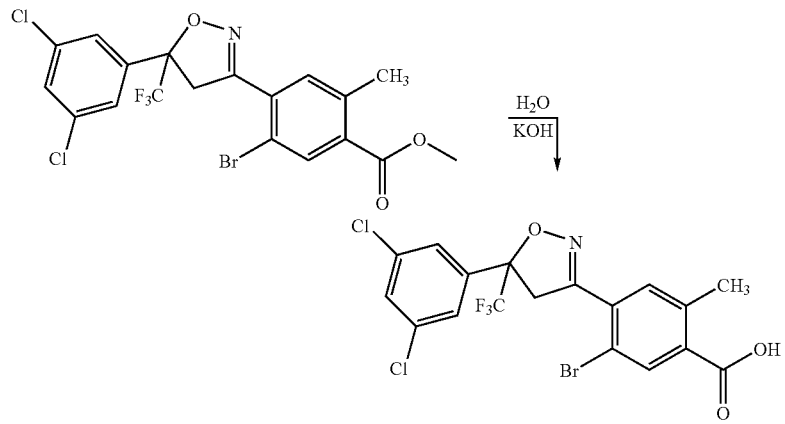

To a solution of 5-bromo-4-[5-(3,5-dichloro-phenyl)-5-trifluoromethyl-4,5-dihydro-isoxazol-3-yl]-2-methyl-benzoic acid methyl ester (Example I22) (290 mg) in tetrahydrofuran (3 ml) was added a solution of potassium hydroxide (1.53 g) in methanol (3 ml) and water (3 ml). The reaction mixture was stirred at ambient temperature for 2 hours. The reaction mixture was acidified by addition of aqueous hydrochloric acid (4N). The aqueous phase was extracted with ethyl acetate (3×10 ml). The combined organic extracts were washed with water (3×10 ml) and brine, dried over sodium sulfate, and concentrated to afford 5-bromo-4-[5-(3,5-dichloro-phenyl)-5-trifluoromethyl-4,5-dihydro-isoxazol-3-yl]-2-methyl-benzoic acid (220 mg) as a white foam. $^1$H-NMR (CDCl$_3$, 400 MHz): 8.20 (s, 1H), 7.30-7.50 (m, 4H), 4.20 (d, 1H), 3.80 (d, 1H), 2.50 (s, 3H).

Similarly, 5-chloro-4-[5-(3,5-dichloro-phenyl)-5-trifluoromethyl-4,5-dihydro-isoxazol-3-yl]-2-methyl-benzoic acid was obtained from 5-chloro-4-[5-(3,5-dichloro-phenyl)-5-trifluoromethyl-4,5-dihydro-isoxazol-3-yl]-2-methyl-benzoic acid methyl ester (Example I22). $^1$H-NMR (CDCl$_3$, 400 MHz): 8.05 (s, 1H), 7.55 (s, 1H), 7.42 (s, 2H), 7.38 (s, 1H), 4.20 (d, 1H), 3.80 (d, 1H), 2.55 (s, 3H).

Example P1

Preparation of 4-[5-(3,5-dichloro-phenyl)-5-trifluoromethyl-4,5-dihydro-isoxazol-3-yl]-2-methyl-N-(3-methyl-thietan-3-yl)-benzamide (Compound No. A1 of Table A)

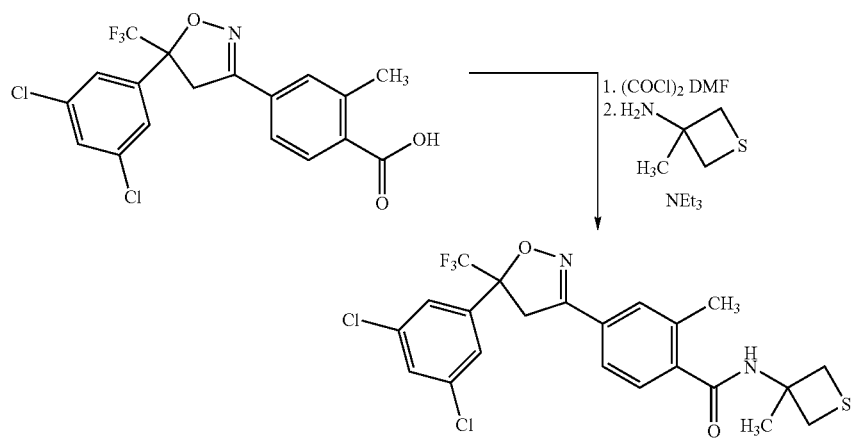

To a solution of 4-[5-(3,5-dichloro-phenyl)-5-trifluoromethyl-4,5-dihydro-isoxazol-3-yl]-2-methyl-benzoic acid (0.5 g) (Example I5) in dichloromethane (3 ml) was added oxalyl chloride (0.122 ml). After addition of N,N-dimethylformamide ("DMF") (2 drops) the reaction mixture was stirred at ambient temperature for 18 hours. The reaction mixture was concentrated to give the acid chloride as a yellow solid, which was used without further purification. Triethylamine (0.05 ml) and 3-methyl-thietan-3-ylamine (28 mg) (prepared according to WO 2007/080131) were added to a solution of the acid chloride (100 mg) in toluene (4 ml). The reaction mixture was stirred at ambient temperature for 2 hours. The reaction mixture was diluted with water and ethyl acetate and the phases were separated. The organic phase was washed twice with water, dried over sodium sulfate and concentrated. The residue was purified by preparative HPLC to give Compound No. A1 of Table A (118 mg) as a colorless solid. $^1$H-NMR (CDCl$_3$, 400 MHz): 7.55-7.45 (m, 6H), 5.90 (s, 1H), 4.05 (d, 1H), 3.85 (d, 2H), 3.70 (d, 1H), 3.10 (d, 2H), 2.50 (s, 3H), 1.85 (s, 3H) ppm.

Similarly, 2,2-dimethyl-thietan-3-ylamine (prepared according to WO 2007/080131), 2,2,4,4-tetramethyl-thietan-3-ylamine (prepared according to WO 2007/080131), thietan-3-ylamine (prepared according to WO 2007/080131), 3-(aminomethyl)-azetidine-1-carboxylic acid tert-butyl ester (CAS RN 325775-44-8, commercially available), and 1-(benzyl)-2-azetidinemethanamine (CAS RN 46193-94-6, commercially available) were used instead of 3-methyl-thietan-3-ylamine to obtain Compound Nos. A2, A3 and A4 of Table A, and Compound Nos. B1 and B2 of Table B, respectively.

Similarly, 4-[5-(3,5-dichloro-phenyl)-5-trifluoromethyl-4,5-dihydroisoxazol-3-yl]-2-trifluoromethyl-benzoic acid (Example I14), 2-bromo-4-[5-(3,5-dichloro-phenyl)-5-trifluoromethyl-4,5-dihydro-isoxazol-3-yl]-benzoic acid (Example I14), and 2-cyano-4-[5-(3,5-dichloro-phenyl)-5-trifluoromethyl-4,5-dihydro-isoxazol-3-yl]-benzoic acid (Example I14) were used instead of 4-[5-(3,5-dichloro-phenyl)-5-trifluoromethyl-4,5-dihydro-isoxazol-3-yl]-2-methyl-benzoic acid to obtain Compound Nos. A14-A19 of Table A, respectively.

Similarly, 4-[5-(3-trifluoromethyl-phenyl)-5-trifluoromethyl-4,5-dihydro-isoxazol-3-yl]-2-methyl-benzoic acid (Example I19) and 4-[5-(3,5-bis-trifluoromethyl-phenyl)-5-trifluoromethyl-4,5-dihydro-isoxazol-3-yl]-2-methyl-benzoic acid (Example I19) were used instead of 4-[5-(3,5-dichloro-phenyl)-5-trifluoromethyl-4,5-dihydro-isoxazol-3-yl]-2-methyl-benzoic acid to obtain Compound Nos. A20, A21, A23, and A24 of Table A, respectively.

Similarly, 4-[5-(3,5-dichloro-phenyl)-5-trifluoromethyl-4,5-dihydro-isoxazol-3-yl]-2-bromo-6-methyl-benzoic acid (Example I20), 4-[5-(3,5-dichloro-phenyl)-5-trifluoromethyl-4,5-dihydro-isoxazol-3-yl]-2-iodo-6-methyl-benzoic acid (Example I20), 5-bromo-4-[5-(3,5-dichloro-phenyl)-5-trifluoromethyl-4,5-dihydro-isoxazol-3-yl]-2-methyl-benzoic acid (Example I22) and 5-chloro-4-[5-(3,5-dichloro-phenyl)-5-trifluoromethyl-4,5-dihydro-isoxazol-3-yl]-2-methyl-benzoic acid (Example I22) were used instead of 4-[5-(3,5-dichloro-phenyl)-5-trifluoromethyl-4,5-dihydro-isoxazol-3-yl]-2-methyl-benzoic acid to obtain Compound Nos. C1-C4 of Table C, respectively.

Example P2

Preparation of 4-[5-(3,5-dichloro-phenyl)-5-trifluoromethyl-4,5-dihydro-isoxazol-3-yl]-2-methyl-N-(3-methyl-1-oxo-thietan-3-yl)-benzamide (Compounds No. A6 and A7 of Table A) and 4-[5-(3,5-dichloro-phenyl)-5-trifluoromethyl-4,5-dihydro-isoxazol-3-yl]-2-methyl-N-(3-methyl-1,1-dioxo-thietan-3-yl)-benzamide (Compound No. A5 of Table A)

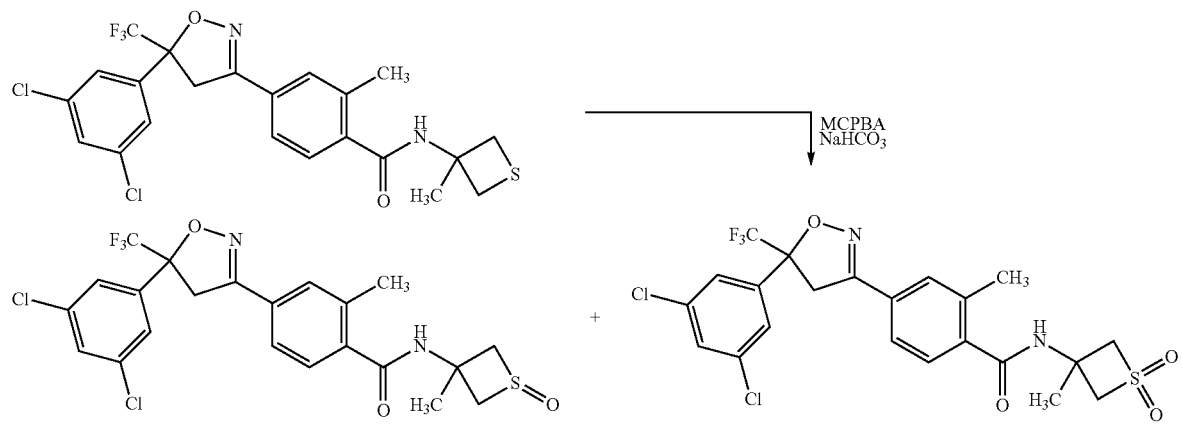

To a solution of 4-[5-(3,5-dichloro-phenyl)-5-trifluoromethyl-4,5-dihydro-isoxazol-3-yl]-2-methyl-N-(3-methyl-thietan-3-yl)-benzamide (Example P1) (81 mg) in dichloromethane (6 ml) was added a solution of sodium hydrogen carbonate (81 mg) in water (2 ml). A solution of 3-chloroperbenzoic acid ("MCPBA") (40 mg) in dichloromethane (1 ml) was added dropwise at 0° C. The reaction mixture was stirred at 0° C. for 30 minutes and at ambient temperature for 3 hours. The reaction mixture was extracted twice with dichloro-methane. The combined organic phases were washed with brine, dried over sodium sulfate and concentrated. The residue was purified by preparative HPLC to give Compound No. A6 of Table A (48 mg), Compound No. A7 of Table A (12 mg) and Compound No. A5 of Table A (16 mg), all as colorless solids.

Compound No. A6 of Table A. $^1$H-NMR (CDCl$_3$, 400 MHz): 7.55-7.35 (m, 6H), 6.05 (s, 1H), 4.10 (d, 1H), 3.95 (d, 2H), 3.65 (d, 2H), 3.60 (d, 2H), 2.45 (s, 3H), 1.60 (s, 3H) ppm.

Compound No. A7 of Table A. $^1$H-NMR (CDCl$_3$, 400 MHz): 7.55-7.45 (m, 6H), 6.00 (s, 1H), 4.25 (d, 2H), 4.05 (d, 1H), 3.65 (d, 1H), 3.25 (d, 2H), 2.45 (s, 3H), 1.80 (s, 3H) ppm.

Compound No. A5 of Table A. $^1$H-NMR (CDCl$_3$, 400 MHz): 7.55-7.45 (m, 6H), 6.20 (s, 1H), 4.50 (d, 2H), 4.20 (d, 1H), 4.05 (d, 2H), 3.70 (d, 1H), 2.45 (s, 3H), 1.90 (s, 3H) ppm.

The following compounds were made using the same method: Compound Nos. A8-A10, A11-A12, A22 and A25 of Table A.

Example P3

Preparation of 4-[5-(3,5-dichloro-phenyl)-5-trifluoromethyl-4,5-dihydro-isoxazol-3-yl]-2-methyl-N-(1-oxo-1-(2,2,2-trifluoro-acetylimino)-thietan-3-yl)-benzamide

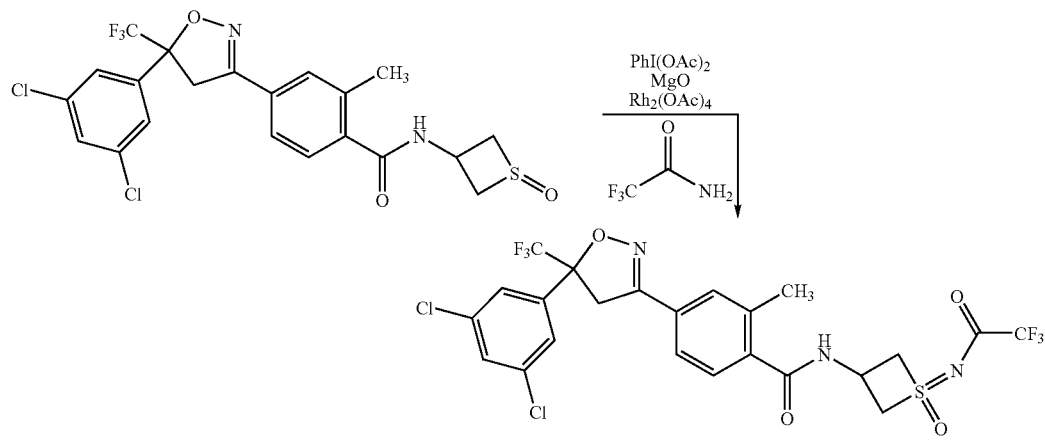

To a solution of 4-[5-(3,5-dichloro-phenyl)-5-trifluoromethyl-4,5-dihydro-isoxazol-3-yl]-2-methyl-N-(1-oxo-thietan-3-yl)-benzamide (Example P2) (0.2 g) in dichloromethane (20 ml) was added trifluoroacetamide (0.09 g), rhodium(II) acetate dimer (0.02 g), magnesium oxide (0.07 g) and iodobenzene diacetate (0.19 g). The reaction mixture was stirred at ambient temperature for 42 hours. The reaction mixture was concentrated and the residue purified by chromatography on silica gel (eluent: ethyl acetate/heptane 1:1) to give 4-[5-(3,5-dichloro-phenyl)-5-trifluoromethyl-4,5-dihydro-isoxazol-3-yl]-2-methyl-N-[1-oxo-1-(2,2,2-trifluoro-acetylimino)-thietan-3-yl]-benzamide (0.06 g) as an off-white powder. HPLC-MS: RT 2.14 min and 2.18 min (two isomers) MH+ 616.

Example P4

Preparation of 4-[5-(3,5-dichloro-phenyl)-5-trifluoromethyl-4,5-dihydro-isoxazol-3-yl]-N-(1-imino-1-oxo-thietan-3-yl)-2-methyl-benzamide (Compound No. A13 of Table A)

To a solution of 4-[5-(3,5-dichloro-phenyl)-5-trifluoromethyl-4,5-dihydro-isoxazol-3-yl]-2-methyl-N-[1-oxo-1-(2,2,2-trifluoro-acetylimino)-thietan-3-yl]-benzamide (Example P3) (0.05 g) in methanol (5 ml) was added potassium carbonate (0.06 g). The reaction mixture was stirred at ambient temperature for 4 hours. Water (0.5 ml) was added and the reaction mixture was concentrated and the residue purified by chromatography on silica gel (eluent: dichloromethane/methanol 9:1) to give Compound No. A13 of Table A (0.02 g) as an amorphous solid. $^1$H-NMR (CDCl$_3$, 400 MHz): 7.85 (d, 1H), 7.45-7.55 (m, 6H), 6.95 (d, 1H), 4.1-4.9 (m, 6H), 4.05 (d, 1H), 3.7 (d, 1H), 2.9-3.2 (m, 2H), 2.45 (s, 3H) ppm.

The following method was used for HPLC-MS analysis:
Method (Agilent 1100 LC) with the following HPLC gradient conditions (Solvent A: 0.05% of formic acid in water and Solvent B: 0.04% of formic acid in acetonitrile/methanol 4:1)

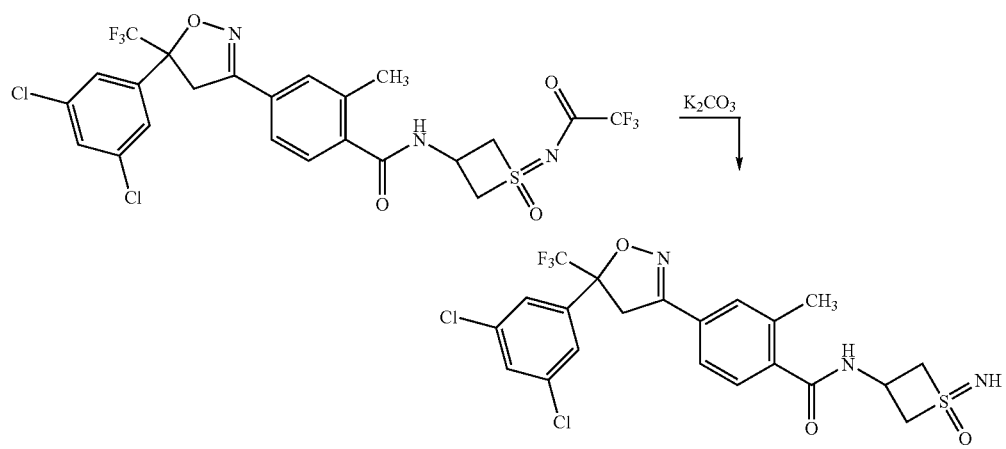

| Time (minutes) | A (%) | B (%) | Flow rate (ml/min) |
|---|---|---|---|
| 0 | 95 | 5 | 1.7 |
| 2.0 | 0 | 100 | 1.7 |
| 2.8 | 0 | 100 | 1.7 |
| 2.9 | 95 | 5 | 1.7 |
| 3.1 | 95 | 5 | 1.7 |

Type of column: Phenomenex Gemini C18; Column length: 30 mm; Internal diameter of column: 3 mm; Particle Size: 3 micron; Temperature: 60° C.

The characteristic values obtained for each compound were the retention time ("RT", recorded in minutes) and the molecular ion, typically the cation $MH^+$ as listed in Table A, Table B and Table C.

TABLE A

Compounds of formula (Ia):

| Comp No. | $R^3$ | $R^4$ | $R^5$ | $R^2$ | $Y^1$ | $Y^2$ | $Y^3$ | RT (min) | $MH^+$ |
|---|---|---|---|---|---|---|---|---|---|
| A1 | —CF$_3$ | 3,5-dichloro-phenyl- | Me | Me | CH$_2$ | S | CH$_2$ | 2.24 | 503 |
| A2 | —CF$_3$ | 3,5-dichloro-phenyl- | Me | H | C(Me)$_2$ | S | CH$_2$ | 2.28 | 517 |
| A3 | —CF$_3$ | 3,5-dichloro-phenyl- | Me | H | C(Me)$_2$ | S | C(Me)$_2$ | 2.35 | 545 |
| A4 | —CF$_3$ | 3,5-dichloro-phenyl- | Me | H | CH$_2$ | S | CH$_2$ | 2.19 | 489 |
| A5 | —CF$_3$ | 3,5-dichloro-phenyl- | Me | Me | CH$_2$ | SO$_2$ | CH$_2$ | 2.11 | 535 |
| A6 | —CF$_3$ | 3,5-dichloro-phenyl- | Me | Me | CH$_2$ | SO* | CH$_2$ | 2.05 | 519 |
| A7 | —CF$_3$ | 3,5-dichloro-phenyl- | Me | Me | CH$_2$ | SO** | CH$_2$ | 2.05 | 519 |
| A8 | —CF$_3$ | 3,5-dichloro-phenyl- | Me | H | CH$_2$ | SO* | CH$_2$ | 2.01 | 505 |
| A9 | —CF$_3$ | 3,5-dichloro-phenyl- | Me | H | CH$_2$ | SO** | CH$_2$ | 2.01 | 505 |
| A10 | —CF$_3$ | 3,5-dichloro-phenyl- | Me | H | CH$_2$ | SO$_2$ | CH$_2$ | 2.07 | 521 |
| A11 | —CF$_3$ | 3,5-dichloro-phenyl- | Me | H | C(Me)$_2$ | SO* | CH$_2$ | 2.05 | 533 |
| A12 | —CF$_3$ | 3,5-dichloro-phenyl- | Me | H | C(Me)$_2$ | SO** | CH$_2$ | 2.03 | 533 |
| A13 | —CF$_3$ | 3,5-dichloro-phenyl- | Me | H | CH$_2$ | SONH | CH$_2$ | 1.95 | 520 |
| A14 | —CF$_3$ | 3,5-dichloro-phenyl- | —CF$_3$ | Me | CH$_2$ | S | CH$_2$ | 2.16 | 557 |
| A15 | —CF$_3$ | 3,5-dichloro-phenyl- | —CF$_3$ | H | CH$_2$ | S | CH$_2$ | 2.08 | 543 |
| A16 | —CF$_3$ | 3,5-dichloro-phenyl- | —Br | Me | CH$_2$ | S | CH$_2$ | 2.22 | 569 |
| A17 | —CF$_3$ | 3,5-dichloro-phenyl- | —Br | H | CH$_2$ | S | CH$_2$ | 2.10 | 555 |
| A18 | —CF$_3$ | 3,5-dichloro-phenyl- | —CN | Me | CH$_2$ | S | CH$_2$ | 2.13 | 514 |
| A19 | —CF$_3$ | 3,5-dichloro-phenyl- | —CN | H | CH$_2$ | S | CH$_2$ | 1.85 | 498 |
| A20 | —CF$_3$ | 3-trifluoromethyl-phenyl- | Me | H | CH$_2$ | S | CH$_2$ | 1.89 | 489 |
| A21 | —CF$_3$ | 3,5-bis-(trifluoromethyl)-phenyl- | Me | Me | CH$_2$ | S | CH$_2$ | 2.16 | 571 |
| A22 | —CF$_3$ | 3,5-bis-(trifluoromethyl)-phenyl- | Me | H | CH$_2$ | SO# | CH$_2$ | 1.72 | 573 |
| A23 | —CF$_3$ | 3,5-bis-(trifluoromethyl)-phenyl- | Me | H | CH$_2$ | S | CH$_2$ | 2.06 | 557 |
| A24 | —CF$_3$ | 3-trifluoromethyl-phenyl- | Me | Me | CH$_2$ | S | CH$_2$ | 1.98 | 503 |
| A25 | —CF$_3$ | 3-trifluoromethyl-phenyl- | Me | H | CH$_2$ | SO# | CH$_2$ | 1.53 | 505 |

= Mixture of diastereomer A and diastereomer B;

*= Diastereomer A (absolute stereochemistry unknown);

**= Diastereomer B (absolute stereochemistry unknown).

TABLE B

Compounds of formula (Ib):

(Ib)

| Comp No. | R⁵ | R² | Y¹ | Y² | Y³ | RT (min) | MH⁺ |
|---|---|---|---|---|---|---|---|
| B1 | Me | H | CH₂ | N—CO—OC(CH₃)₃ | CH₂ | 2.21 | 586 |
| B2 | Me | H | N—CH₂—C₆H₅ | CH₂ | CH₂ | 1.54 | 576 |

TABLE C

Compounds of formula (Ic):

(Ic)

| Comp No. | R³ | R⁴ | R⁵ᵃ | R⁵ᵇ | R⁵ᶜ | R⁵ᵈ | M.p. | RT (min) | MH⁺ |
|---|---|---|---|---|---|---|---|---|---|
| C1 | —CF₃ | 3,5-dichlorophenyl- | Me | H | H | Br | 107° C. | 2.20 | 567/569 |
| C2 | —CF₃ | 3,5-dichlorophenyl- | Me | H | H | I | 87° C. | 2.24 | 615/616 |
| C3 | —CF₃ | 3,5-dichlorophenyl- | Me | H | Br | H | 92° C. | 2.22 | 567/569 |
| C4 | —CF₃ | 3,5-dichlorophenyl- | Me | H | Cl | H | 63.5 | 2.22 | 521/522 |

BIOLOGICAL EXAMPLES

This Example illustrates the pesticidal/insecticidal properties of compounds of formula (I). Tests were performed as follows:

*Spodoptera littoralis* (Egyptian Cotton Leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).

The following compounds gave at least 80% control of *Spodoptera littoralis*: A1, A2, A3, A4, A5, A6, A7, A8, A9, A10, A11, A12, A13, A14, A15, A16, A17, A20, A21, A22, A23, A24, A25.

*Heliothis virescens* (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.

The following compounds gave at least 80% control of *Heliothis virescens*: A1, A2, A3, A4, A5, A6, A7, A8, A9, A10, A11, A12, A13, A14, A15, A16, A17, A20, A21, A22, A23, A24, A25, C1, C2, C3, C4.

*Plutella xylostella* (Diamond Back Moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.

The following compounds gave at least 80% control of *Plutella xylostella*: A1, A2, A3, A4, A5, A6, A7, A8, A9, A10, A11, A12, A13, A14, A15, A16, A17, A20, A21, A22, A23, A24, A25, C1, C2, C3, C4.

*Diabrotica balteata* (Corn Root Worm):

A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.

The following compounds gave at least 80% control of *Diabrotica balteata*: A1, A2, A3, A4, A5, A6, A7, A8, A9, A10, A11, A12, A13, A14, A15, A16, A17, A20, A21, A22, A23, A24, A25, B1, C1, C2, C3, C4.

*Thrips tabaci* (Onion Trips):

Sunflower leaf discs were placed on agar in a 24-well microtiter plate and sprayed with test solutions at an application rate of 200 ppm. After drying, the leaf discs were infested with an aphid population of mixed ages. After an incubation period of 7 days, samples were checked for mortality.

The following compounds gave at least 80% control of *Thrips tabaci*: A1, A2, A3, A4, A5, A6, A7, A8, A9, A10, A11, A12, A13, A14, A15, A16, A17, A20, A21, A22, A23, A24, A25, C2, C3, C4.

*Tetranychus urticae* (Two-Spotted Spider Mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compounds gave at least 80% control of *Tetranychus urticae*: A1, A2, A3, A4, A5, A6, A7, A8, A9, A10, A11, A12, A13, A14, A15, A16, A17, A20, A21, A22, A23, A24, A25.

Compound Nos. A18 and A19, and Compound No. B2 of Table B was tested using the same protocols and showed little or no effect on mortality, feeding behavior, or growth regulation under the test conditions.

The invention claimed is:

1. A compound of formula (I)

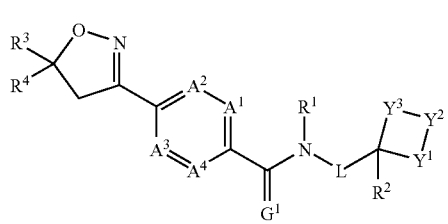

wherein
$A^1$, $A^2$, $A^3$ and $A^4$ are independently of one another C—H, C—$R^5$, or nitrogen;
$G^1$ is oxygen or sulfur;
L is a single bond, $C_1$-$C_8$alkyl, $C_1$-$C_8$haloalkyl, $C_2$-$C_8$alkenyl, $C_2$-$C_8$haloalkenyl, $C_2$-$C_8$alkynyl, or $C_2$-$C_8$haloalkynyl;
$R^1$ is hydrogen, $C_1$-$C_8$alkyl, $C_1$-$C_8$alkylcarbonyl-, or $C_1$-$C_8$alkoxycarbonyl-;
$R^2$ is hydrogen, or $C_1$-$C_8$alkyl;
$R^3$ is $C_1$-$C_8$haloalkyl;
$R^4$ is aryl or aryl substituted by one to three $R^6$, or heterocyclyl or heterocyclyl substituted by one to three $R^6$;
$Y^1$, $Y^2$ and $Y^3$ are independently of another $CR^7R^8$, S, SO, $SO_2$, provided that at least one of $Y^1$, $Y^2$ or $Y^3$ is not $CR^7R^8$;
each $R^5$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, $C_1$-$C_8$alkoxycarbonyl-, aryl or aryl optionally substituted by one to three $R^{10}$, or heteroaryl or heteroaryl optionally substituted by one to three $R^{10}$, or where two $R^5$ are adjacent, the two $R^5$ may together with the carbon atoms to which the two $R^5$ are bonded form a 5-membered ring, wherein the 5-membered ring is —OCH═N—, —SCH═N—, —OCR$^{10}$═N—, or —SCR$^{10}$═N—;
each $R^6$ is independently halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl-;
each $R^7$ and $R^8$ is independently hydrogen, halogen, $C_1$-$C_8$alkyl, or $C_1$-$C_8$haloalkyl;
each $R^{10}$ is independently halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl-; and;
or a salt or N-oxide thereof;
wherein the term "aryl" refers to phenyl, naphthalenyl, anthracenyl, indenyl or phenanthrenyl;
wherein the term "heterocyclyl" refers to heteroaryl and their unsaturated or partially unsaturated analogues; and
wherein the term "heteroaryl" refers to a monocyclic group selected from pyridyl, pyridazinyl, pyrimidinyl, pyrazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl, and thiadiazolyl, or a bicyclic group selected from quinolinyl, cinnolinyl, quinoxalinyl, benzimidazolyl, benzothiophenyl, and benzothiadiazolyl.

2. A compound according to claim 1 wherein $A^1$ is C—$R^5$; $A^2$ is C—H; $A^3$ is C—H; and $A^4$ is C—H and wherein $G^1$ is oxygen.

3. A compound according to claim 1 wherein L is a single bond, $C_1$-$C_8$alkyl, or $C_1$-$C_8$haloalkyl.

4. A compound according to claim 1 wherein $R^1$ is hydrogen, methyl, ethyl, methylcarbonyl-, or methoxycarbonyl-.

5. A compound according to claim 1 wherein $R^2$ is hydrogen or methyl.

6. A compound according to claim 1 wherein $R^3$ is chlorodifluoromethyl or trifluoromethyl.

7. A compound according to claim 1 wherein $R^4$ is phenyl or phenyl substituted by one to three $R^6$.

8. A compound according to claim 1 wherein $Y^2$ is S, SO, or $SO_2$, and $Y^1$ and $Y^3$ are independently of another $CR^7R^8$.

9. A compound according to claim 1 wherein each $R^5$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-.

10. A compound according to claim 1 wherein each $R^7$ and $R^8$ is independently hydrogen or methyl.

11. A compound of formula (XI)

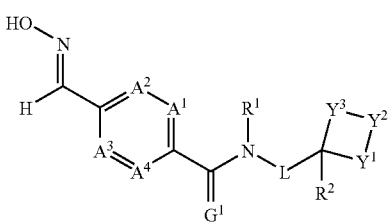

wherein $A^1$, $A^2$, $A^3$, $A^4$, $G^1$, L, $R^1$, $R^2$, $Y^1$, $Y^2$ and $Y^3$ are as defined in claim 1; or a salt or N-oxide thereof; or
a compound of formula (XI')

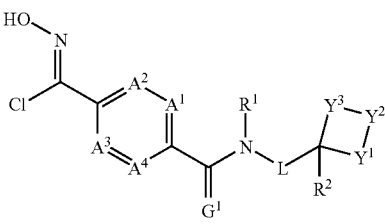

wherein $A^1$, $A^2$, $A^3$, $A^4$, $G^1$, L, $R^1$, $R^2$, $Y^1$, $Y^2$ and $Y^3$ are as defined in claim 1; or a salt or N-oxide thereof; or
a compound of formula (XII)

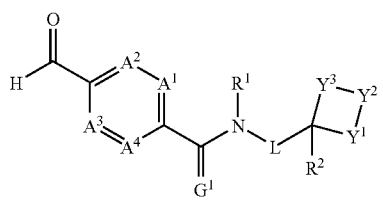

wherein $A^1$, $A^2$, $A^3$, $A^4$, $G^1$, L, $R^1$, $R^2$, $Y^1$, $Y^2$ and $Y^3$ are as defined in claim 1; or a salt or N-oxide thereof; or a compound of formula (XIII)

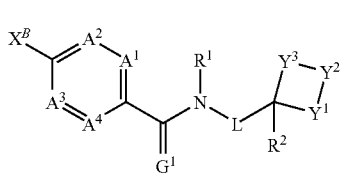

wherein $A^1$, $A^2$, $A^3$, $A^4$, $G^1$, L, $R^1$, $R^2$, $Y^1$, $Y^2$ and $Y^3$ are as defined in claim 1 and $X^B$ is halogen; or a salt or N-oxide thereof; or a compound of formula (XIV)

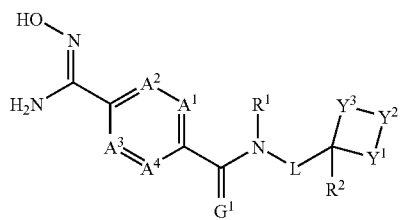

wherein $A^1$, $A^2$, $A^3$, $A^4$, $G^1$, L, $R^1$, $R^2$, $Y^1$, $Y^2$ and $Y^3$ are as defined in claim 1; or a salt or N-oxide thereof; or a compound of formula (XV)

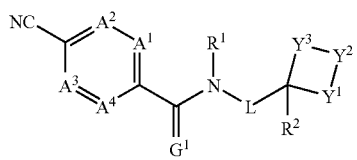

wherein $A^1$, $A^2$, $A^3$, $A^4$, $G^1$, L, $R^1$, $R^2$, $Y^1$, $Y^2$ and $Y^3$ are as defined in claim 1; or a salt or N-oxide thereof; or a compound of formula (XVIII)

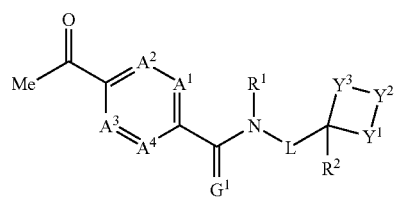

wherein $A^1$, $A^2$, $A^3$, $A^4$, $G^1$, L, $R^1$, $R^2$, $Y^1$, $Y^2$ and $Y^3$ are as defined in claim 1; or a salt or N-oxide thereof; or a compound of formula (XIX)

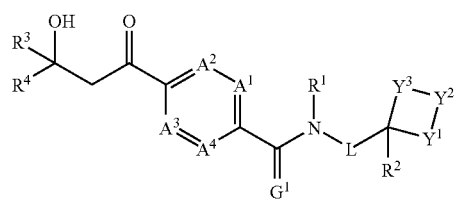

wherein $A^1$, $A^2$, $A^3$, $A^4$, $G^1$, L, $R^1$, $R^2$, $R^3$, $R^4$, $Y^1$, $Y^2$ and $Y^3$ are as defined in claim 1; or a salt or N-oxide thereof; or a compound of formula (XX)

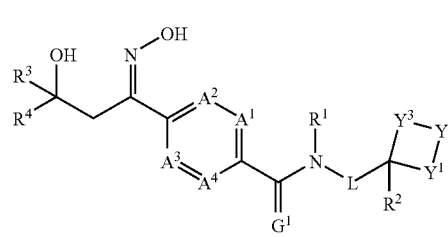

wherein $A^1$, $A^2$, $A^3$, $A^4$, $G^1$, L, $R^1$, $R^2$, $R^3$, $R^4$, $Y^1$, $Y^2$ and $Y^3$ are as defined in claim 1; or a salt or N-oxide thereof; or a compound of formula (XXII)

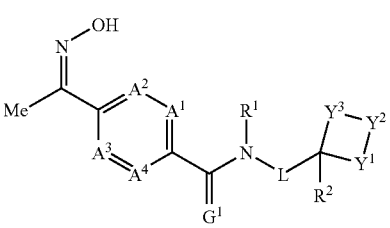

wherein $A^1$, $A^2$, $A^3$, $A^4$, $G^1$, L, $R^1$, $R^2$, $Y^1$, $Y^2$ and $Y^3$ are as defined in claim 1; or a salt or N-oxide thereof; or a compound of formula (XXIII)

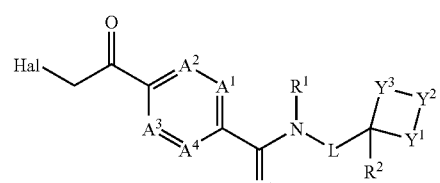

wherein $A^1$, $A^2$, $A^3$, $A^4$, $G^1$, L, $R^1$, $R^2$, $Y^1$, $Y^2$ and $Y^3$ are as defined in claim 1 and Hal is a halogen; or a salt or N-oxide thereof; or a compound of formula (XXIV)

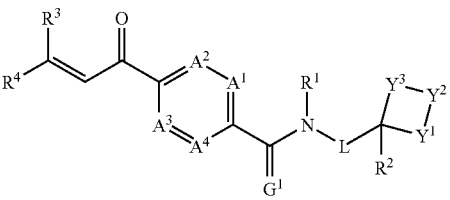

wherein $A^1$, $A^2$, $A^3$, $A^4$, $G^1$, L, $R^1$, $R^2$, $R^3$, $R^4$, $Y^1$, $Y^2$ and $Y^3$ are as defined in claim 1; or a salt or N-oxide thereof; or a compound of formula (XXIV')

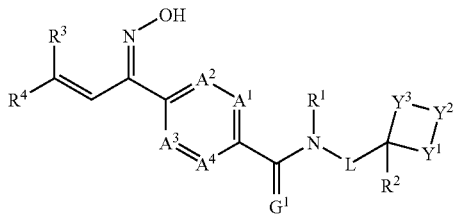

(XXIV')

wherein $A^1, A^2, A^3, A^4, G^1, L, R^1, R^2, R^3, R^4, Y^1, Y^2$ and $Y^3$ are as defined in claim 1; or a salt or N-oxide thereof.

12. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as defined in claim 1.

13. An insecticidal, acaricidal, nematicidal or molluscicidal composition comprising an insecticidally, acaricidally, nematicidally or molluscicidally effective amount of a compound of formula (I) as defined in claim 1, and which can further comprise another compound having biological activity.

14. A compound according to claim 1 or claim 2 wherein L is a single bond or $CH_2$.

15. A compound according to claim 1 wherein $R^4$ is phenyl substituted by one to three $R^6$.

16. A compound according to claim 1 wherein each $R^5$ is independently chloro, fluoro or methyl.

17. A compound according to claim 1 wherein each $R^6$ is independently bromo, chloro, fluoro, cyano, nitro, methyl, ethyl, trifluoromethyl, methoxy, difluoromethoxy, trifluoromethoxy, or methoxycarbonyl.

18. A compound according to claim 1 wherein each $R^6$ is independently bromo, chloro or fluoro.

19. A compound according to claim 1 wherein
$A^1$ is C—$R^5$; $A^2$ is C—H; $A^3$ is C—H; and $A^4$ is C—H;
$G^1$ is oxygen;
L is a single bond or methyl;
$R^1$ is hydrogen;
$R^2$ is hydrogen;
$R^3$ is chlorodifluoromethyl or trifluoromethyl;
$R^4$ is phenyl or phenyl substituted by one to three $R^6$;
$Y^2$ is S, SO, or $SO_2$, and $Y^1$ and $Y^3$ are independently of another $CR^7R^8$;
$R^5$ is bromo, chloro, fluoro, cyano, nitro, methyl, ethyl, trifluoromethyl, methoxy, difluoromethoxy, trifluoromethoxy, or methoxycarbonyl-;
each $R^6$ is independently chloro, fluoro, cyano, nitro, methyl, ethyl, trifluoromethyl, methoxy, or trifluoromethoxy;
each $R^7$ and $R^8$ is independently hydrogen or methyl.

20. A compound according to claim 1 wherein
$A^1$ is C—$R^5$; $A^2$ is C—H; $A^3$ is C—H; and $A^4$ is C—H;
$G^1$ is oxygen;
L is a single bond;
$R^1$ is hydrogen;
$R^2$ is hydrogen;
$R^3$ is trifluoromethyl;
$R^4$ is phenyl substituted by one to three $R^6$;
$Y^2$ is S, SO, or $SO_2$, and $Y^1$ and $Y^3$ are independently of another $CR^7R^8$;
$R^5$ is chloro, fluoro or methyl;
each $R^6$ is independently bromo, chloro or fluoro;
each $R^7$ and $R^8$ is independently hydrogen.

21. A compound of formula Ia

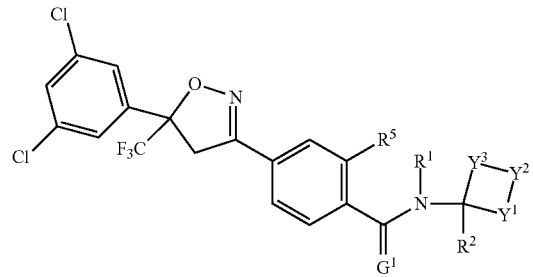

(Ia)

wherein $G^1$ is oxygen, $R^1$ is hydrogen, $R^2$ is hydrogen, $R^5$ is methyl, $Y^1$ is $CH_2$, $Y^2$ is S, SO or $SO_2$, and $Y^3$ is $CH_2$.

* * * * *